(12) United States Patent
Liu et al.

(10) Patent No.: US 8,821,811 B2
(45) Date of Patent: Sep. 2, 2014

(54) IN-VITRO CONTACT LENS TESTING

(71) Applicant: Google Inc., Mountain View, CA (US)

(72) Inventors: Zenghe Liu, Alameda, CA (US); James Etzkorn, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 13/627,727

(22) Filed: Sep. 26, 2012

(65) Prior Publication Data
US 2014/0087452 A1    Mar. 27, 2014

(51) Int. Cl.
*G01N 21/75* (2006.01)
*C12M 1/34* (2006.01)
*C12M 3/00* (2006.01)

(52) U.S. Cl.
CPC ....... *G01N 21/75* (2013.01); *B01J 2219/00621* (2013.01); *B01J 2219/00612* (2013.01)
USPC .......... 422/425; 422/401; 422/82.05; 436/95; 436/165; 435/287.1; 600/347

(58) Field of Classification Search
CPC .............. B01J 2219/00612; B01J 2219/00621
USPC ................. 422/401, 425, 82.05; 436/95, 165; 435/287.1; 600/347
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Bionic contact lens 'to project emails before eyes,' http://www.kurzweilai.netforums/topic/bionic-contact-lens-to-project-emails-before-eyes, Last accessed Mar. 14, 2012, 2 pages.

(Continued)

*Primary Examiner* — Lyle Alexander
(74) *Attorney, Agent, or Firm* — McDonnell Boehnen Hulbert & Berghoff LLP

(57) ABSTRACT

Contact lens testing apparatuses and method for testing contact lenses for analytes are presented. In an aspect, a device is provided that includes a housing configured to hold one or more contact lenses, and a testing compartment provided within the housing and comprising a reagent, the reagent configured to facilitate a chemical reaction in response to the existence of a predetermined biomarker disposed on or within a contact lens placed in the testing compartment, wherein the chemical reaction produces a known result related to state information of an individual from which the biomarker was generated.

12 Claims, 21 Drawing Sheets

(56) References Cited

U.S. PATENT DOCUMENTS

| | | |
|---|---|---|
| 4,463,149 A | 7/1984 | Ellis |
| 4,526,178 A | 7/1985 | Opel |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,869,231 A | 2/1999 | Romisch et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,462 B2 * | 9/2008 | Morris et al. ............... 435/14 |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0027240 A1 * | 2/2003 | Asher et al. ............... 435/25 |
| 2003/0045783 A1 | 3/2003 | March et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 * | 10/2005 | Rozakis et al. ............... 435/4 |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |

(56) References Cited

U.S. PATENT DOCUMENTS

| | | | |
|---|---|---|---|
| 2012/0177576 | A1 | 7/2012 | Hu |
| 2012/0201755 | A1 | 8/2012 | Rozakis et al. |
| 2012/0245444 | A1 | 9/2012 | Otis et al. |
| 2012/0259188 | A1 | 10/2012 | Besling |
| 2013/0338039 | A1* | 12/2013 | Mazed et al. ............... 506/16 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 7/2004 |
| WO | 2004/080297 | 9/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Brahim, et al., "Polypyrrole-hydrogel composites for the construction of clinically important biosensors," 2002, Biosensors & Bioelectronics, pp. 53-59, vol. 17.
Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.
Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Holloway, "Microsoft developing electronic contact lens to monitor blood sugar," Gizmag, Jan. 5, 2012, http:// www.gizmag.com/microsoft-electronic-diabetic-contact-lens/20987/, Last accessed Mar. 13, 2012. 5 pages.
Huang, et al., "Wrinkling of Ultrathin Polymer Films," Mater. Res. Soc. Symp. Proc., 2006, 6 pages, vol. 924, Materials Research Society.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Liao, et al., "A 3µW CMOS Glucose Sensor for Wireless Contact-Lens Tear Glucose Monitoring," IEEE Journal of Solid-State Circuits, Jan. 2012, pp. 335-344, vol. 47, No. 1.
Liao, et al., "A 3-µW Wirelessly Powered CMOS Glucose Sensor for an Active Contact Lens," 2011 IEEE International Solid-State Circuits Conference, Session 2, Feb. 21, 2011, 3 paages.
Lingley, et al., "A Single-Pixel Wireless Contact Lens Display," Journal of Micromechanics and Microengineering, 2011, pp. 1-8.
Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions On Biomedical Circuits and Systems, Dec. 2010, pp. 454-461, vol. 4, No. 6.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.

(56) References Cited

OTHER PUBLICATIONS

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 4 pages.

International Searching Authority, International Search Report and Written Opinion for PCT/US2013/060432 mailed Dec. 23, 2013, 12 pages.

* cited by examiner

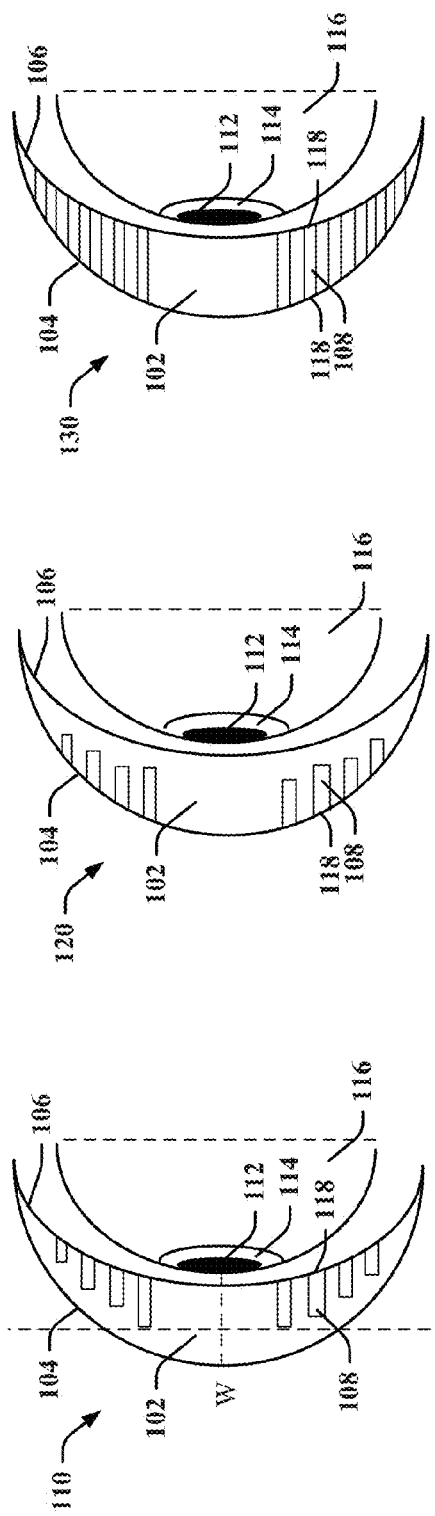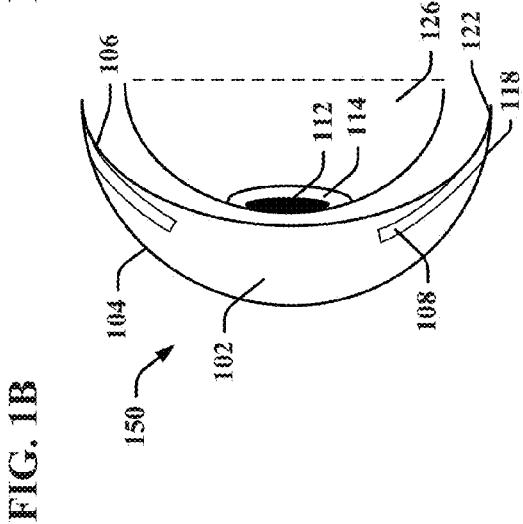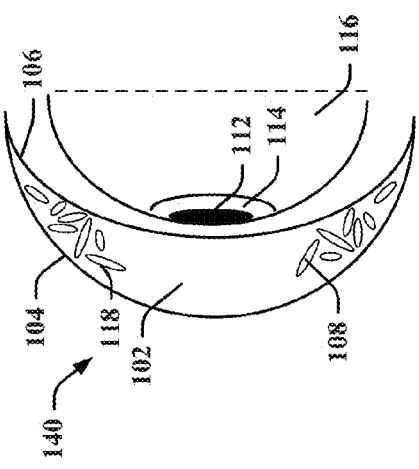

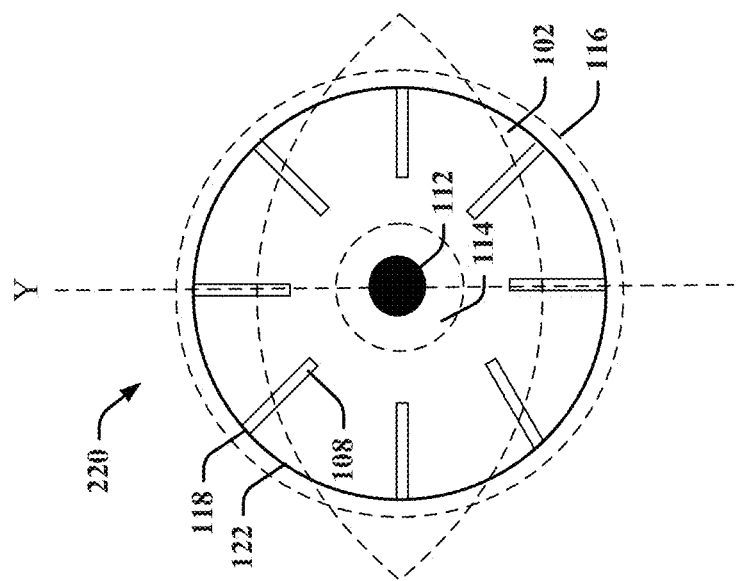
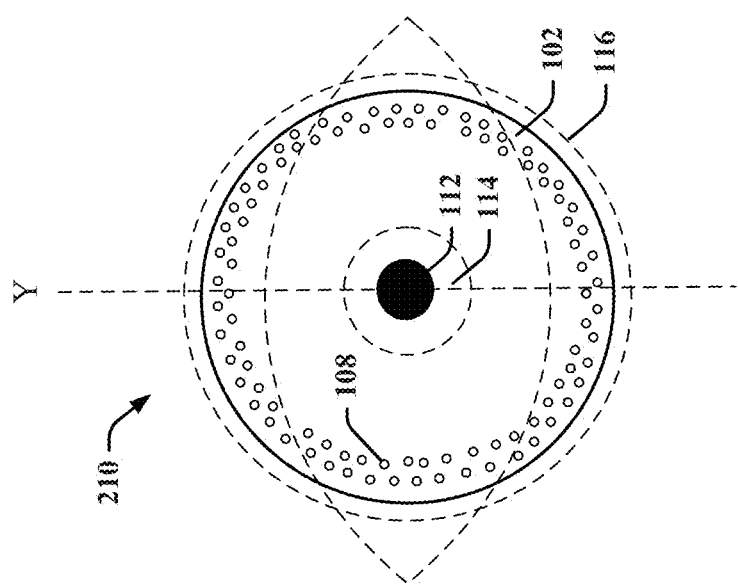

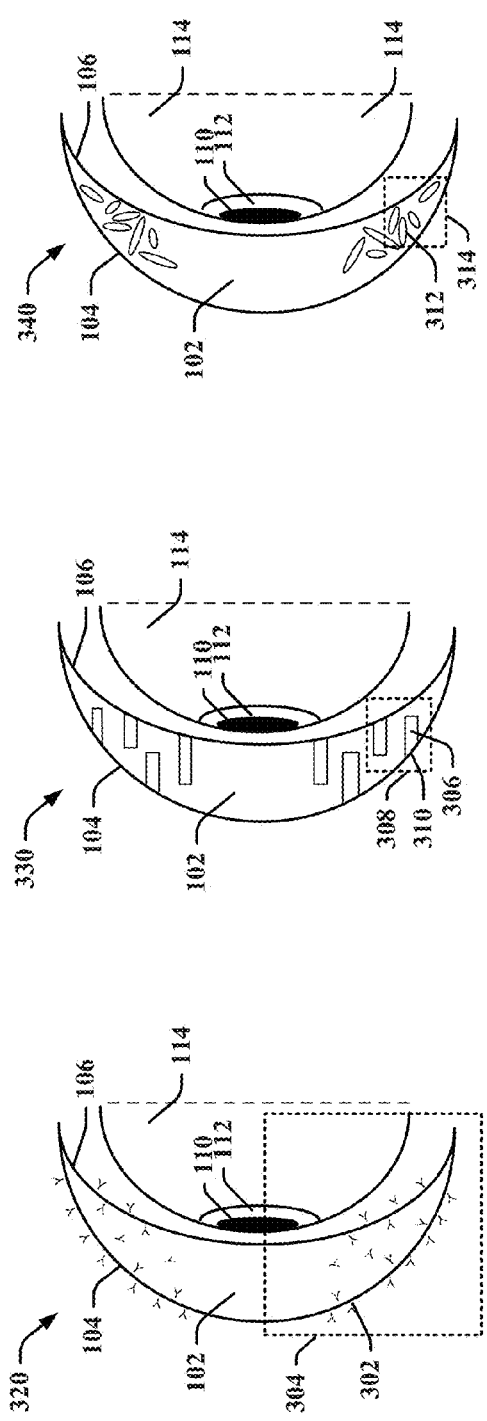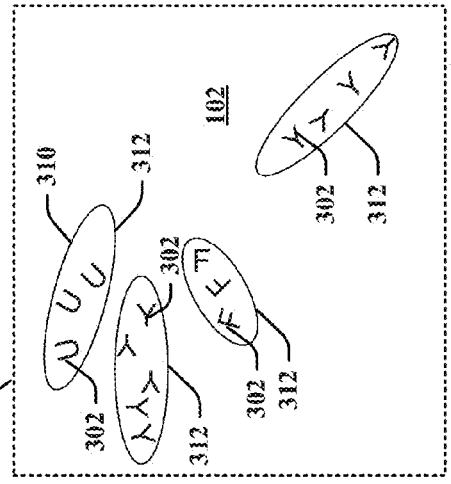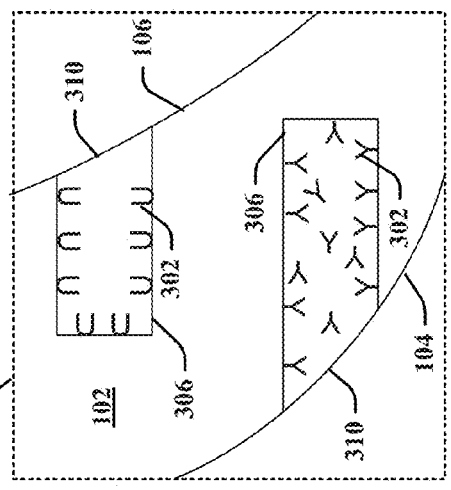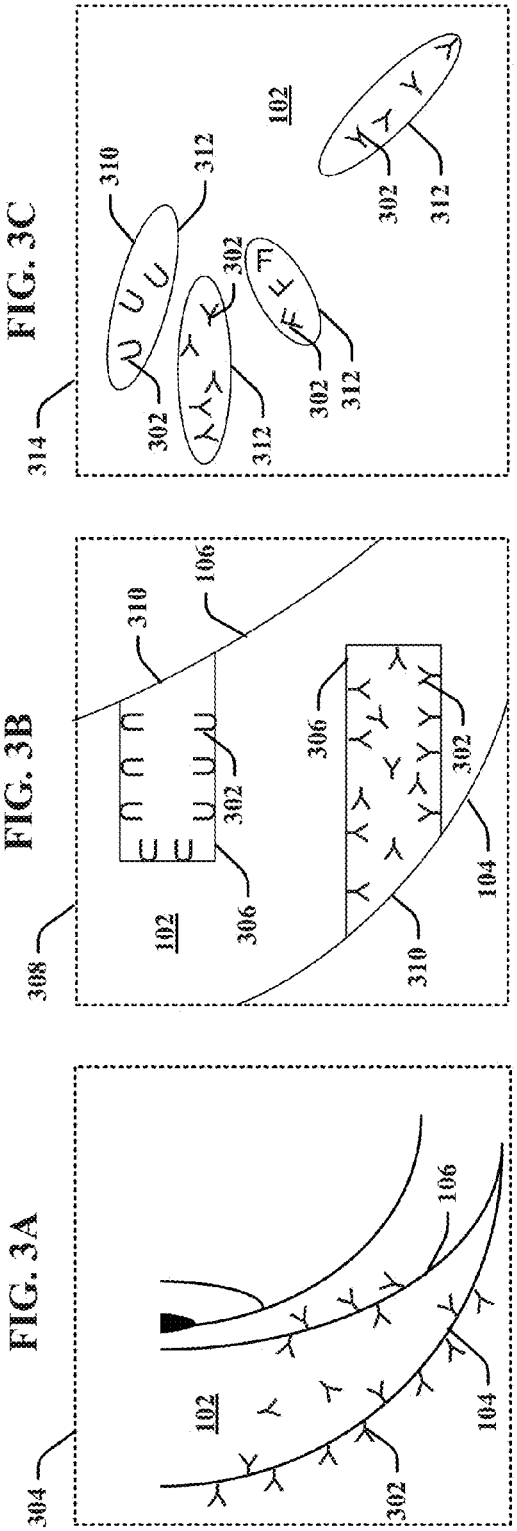

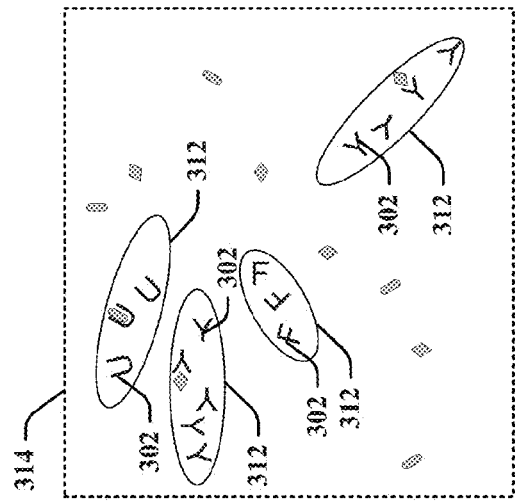
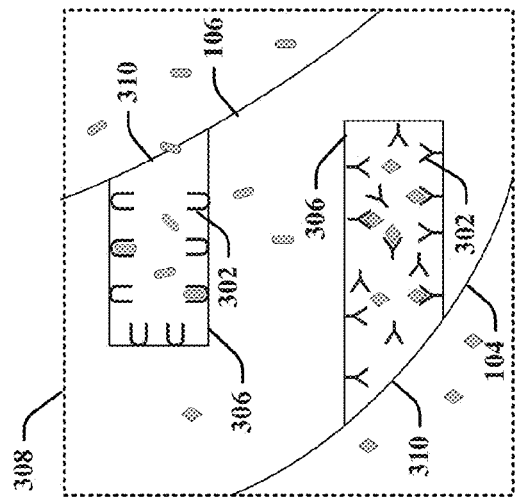
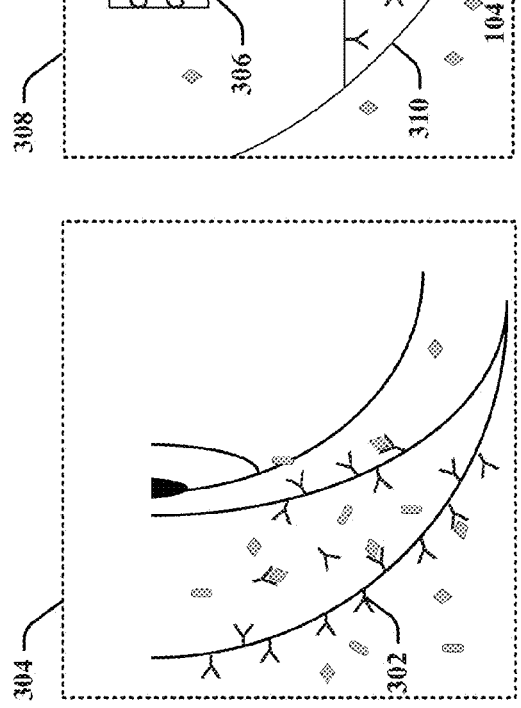
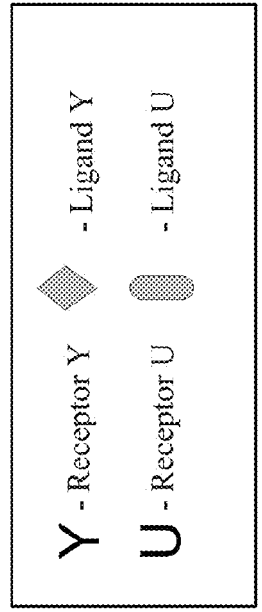
FIG. 4A   FIG. 4B   FIG. 4C

1700

INSERTING A CONTACT LENS INTO AN EYE, THE CONTACT LENS COMPRISING ONE OR MORE RECEPTORS DISPOSED ON OR WITHIN A SUBSTRATE OF THE CONTACT LENS, THE ONE OR MORE RECEPTORS ARE CONFIGURED TO BIND TO A KNOWN LIGAND  1702

RECEIVING ONE OR MORE KNOWN LIGANDS AT THE ONE OR MORE RECEPTORS, WHEREIN THE RECEIVED LIGANDS BIND TO THE ONE OR MORE RECEPTORS 1704

REMOVING THE CONTACT LENS FROM THE EYE WITH THE ONE OR MORE KNOWN LIGANDS BOUND TO THE ONE OR MORE RECEPTORS  1706

FIG. 17

IN-VITRO CONTACT LENS TESTING

CROSS REFERENCES TO RELATED APPLICATIONS

This application is related to co-pending U.S. patent application Ser. No. 13/627,710, which was filed on Sep. 26, 2012 and co-pending U.S. patent application Ser. No. 13/627,742 which was filed on Sep. 26, 2012.

TECHNICAL FIELD

This disclosure generally relates to contact lenses that collect tear samples and/or contact lenses that have integrated receptors for binding known ligands and testing of such contact lenses.

BACKGROUND

Tear fluid provides a viable source of biological analytes that can indicate various health states of the individual from which the tear fluid is generated. However, collection of tear samples for testing is difficult. Many processes for collecting tear samples usually irritate the eye and produce tear fluid having constituents which lead to erroneous test results. For example, tear fluid generated from irritation of eye, such as touching of the eye and tear fluid generated from an emotional reaction comprise different constituents than basal tears and are generally produced in greater quantity than basal tears. Such reflex and emotional tears interfere with the composition of tear samples of interest.

BRIEF DESCRIPTION OF THE DRAWINGS

FIG. 1A illustrates an exemplary, non-limiting embodiment of a contact lens that collects tear fluid.

FIG. 1B illustrates another exemplary, non-limiting embodiment of a contact lens that collects tear fluid.

FIG. 1C illustrates another exemplary, non-limiting embodiment of a contact lens that collects tear fluid.

FIG. 1D illustrates another exemplary, non-limiting embodiment of a contact lens that collects tear fluid.

FIG. 1E illustrates another exemplary, non-limiting embodiment of a contact lens that collects tear fluid.

FIG. 2A illustrates another exemplary, non-limiting embodiment of a contact lens that collects tear fluid.

FIG. 2B illustrates another exemplary, non-limiting embodiment of a contact lens that collects tear fluid.

FIG. 3A illustrates an exemplary, non-limiting embodiment of a contact lens that includes one or more receptors for detecting a known ligand.

FIG. 3B illustrates another exemplary, non-limiting embodiment of a contact lens that includes one or more receptors for detecting a known ligand.

FIG. 3C illustrates another exemplary, non-limiting embodiment of a contact lens that includes one or more receptors for detecting a known ligand.

FIG. 3D illustrates a magnified view of an exemplary, non-limiting embodiment of a contact lens that includes one or more receptors for detecting a known ligand.

FIG. 3E illustrates another magnified view of an exemplary, non-limiting embodiment of a contact lens that includes one or more receptors for detecting a known ligand.

FIG. 3F illustrates another magnified view of an exemplary, non-limiting embodiment of a contact lens that includes one or more receptors for detecting a known ligand.

FIG. 4A illustrates a magnified view of an exemplary, non-limiting embodiment of a contact lens that includes one or more receptors bound to a known ligand in vivo.

FIG. 4B illustrates another magnified view of an exemplary, non-limiting embodiment of a contact lens that includes one or more receptors bound to a known ligand in vivo.

FIG. 4C illustrates another magnified view of an exemplary, non-limiting embodiment of a contact lens that includes one or more receptors bound to a known ligand in vivo.

FIG. 17 illustrates an example methodology for capturing a known ligand at a receptor integrated within a contact lens in accordance with various aspects and implementations described herein.

DETAILED DESCRIPTION

Figure 5:
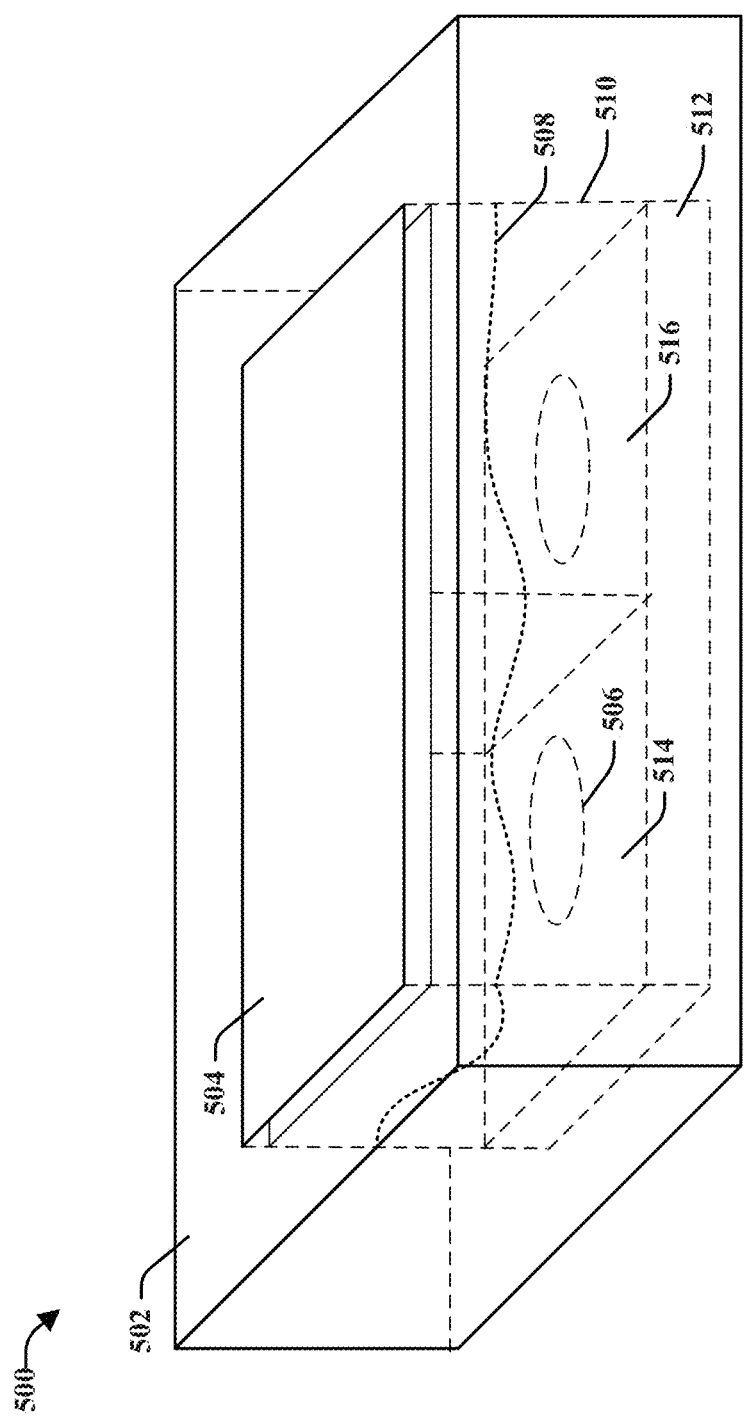
FIG. 5 is an illustration of a block diagram of an exemplary, non-limiting apparatus that facilitates testing of contact lenses.

By way of introduction, the subject matter disclosed herein relates to contact lenses that facilitate testing for substances, such as biomarkers, received thereon and/or therein following wear of the contact lenses. In particular, contact lenses are described that are configured to collect tear fluid in one or more cavities provided therein. In accordance with an aspect, contact lenses can be integrated with one or more receptors for binding a known ligand. The subject matter further relates to methods and apparatuses for testing and manufacturing such contact lenses.

In one or more aspects, a contact lens collects tear fluid over time so as to not disturb normal functions of the eye. The contact lens contains multiple micro-cavities that fill with tear fluid throughout the day so as to not dry out the eye or cause irritation. The contact lens can later be removed and analyzed by an apparatus to extract tear fluid for subsequent testing thereof. The apparatus can be used to test any suitable contact lens, with fluid collection capabilities, that has been worn for an extended period of time. This apparatus can measure important health indicators (e.g., sugar levels, cholesterol levels, alcohol levels, contaminants, allergens, bacteria, viruses, hormones, . . . ) of the user as a function of the collected tear fluid without requiring blood to be drawn.

In some aspects, one or more receptors are provided on and/or within a contact lens. For example, one or more receptors can be provided within the cavities that are configured to collect tear fluid. Receptors can be selected that are known to bind to a known ligand. For example, a receptor may include an antibody having an affinity for a known antigen. Therefore, if the known ligand is present within the eye environment and/or tear fluid of the wearer of the contact lens, it will bind to the receptor. Later, the contact lens can be provided to a testing apparatus that can apply a ligand binding assay to detect the presence and/or quantity of the ligand on or within the worn contact lens. The testing apparatus can further determine state information about the wearer of the contact lens based on the results of the ligand binding assay.

Manufacturing methods for creating the above noted tear collecting and/or bio-conjugated contact lenses are further provided. In a first embodiment, material that the lens is made out of, for example silicone hydrogel, is injected into a contact lens mold. This contact lens mold contains a series of needles that the hydrogel flows around. Then the material is cured (e.g. with ultraviolent (UV) light), the contact lens mold is removed, and micro-channels are formed where the needles were. In a second embodiment, rods are formed out of a polymer such as photoresist or PMMA. In an aspect, the rods can be placed inside a contact lens mold and then gel can be injected into the contact lens mold so as to cover the rods. In another aspect, a gel can be injected into a contact lens mold and the rods can then be injected into the gel. Then the gel with the rods therein is cured and the cured gel is removed from the contact lens mold. The rods can further be dissolved using a solvent that does not harm the lens material. A third embodiment involves a two step contact lens molding process. A top half of the lens is first molded over a substrate that has peaks or bumps. The bottom half of the lens includes a substrate having a substantially flat cross-section. The top half and bottom half are then combined so that channels are created in the center of the lens.

Various aspects are now described with reference to the drawings, wherein like reference numerals are used to refer to like elements throughout. It should be appreciated that one or more aspects of the drawings from FIGS. 1A-13 are not drawn to scale. In the following description, for purposes of explanation, numerous specific details are set forth in order to provide a more thorough understanding of one or more aspects. It should be evident, however, that such aspects can be practiced without these specific details. In other instances, structures and devices are shown in block diagram form in order to facilitate describing one or more aspects.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received, or transmitted data.

FIGS. 1A-1E and 2A-2B illustrate exemplary non-limiting embodiments of contact lenses that facilitate collecting tear fluid. Such contact lenses facilitate collection and analysis of one or more biological features associated with a wearer of the contact lens where the biological features are located within tear fluid generated by the wearer of the contact lens. FIGS. 2A and 2B illustrate top planar views of example contact lenses and FIGS. 1A-1E illustrate cross-sectional views of example contact lenses taken along access Y of FIG. 2A or 2B. Each of the contact lenses depicted in FIGS. 1A-1E and 2A-2B comprise one or more cavities 108 that collect tear fluid over time when worn by an individual on/in his or her eye. For example, the cavities 108 may fill with tear fluid via capillary action and/or osmosis. Such tear collecting contact lenses may be disposable lenses that are configured for single use. In another aspect, contact lenses disclosed herein may be configured for repeated use.

Cavities provided within the subject tear fluid collecting contact lenses can fill with tear fluid over a period of time dependant on the size and shape of the cavities. Further, tear collecting cavities provided within contact lenses disclosed herein can slowly fill with tear fluid over time so as not to dry out the eye. In an aspect, one or more cavities provided within a contact lens fill with tear fluid over a period of about twenty four hours. It is to be appreciated that the contact lens can be designed and configured to collect tear fluid over any suitable range of time (e.g., seconds, minutes, hours, days, weeks, or months). In an aspect, the cavities are configured to store collected tear fluid while the contact lens is worn in the eye and when the contact lens is removed from the eye.

The cavities 108 are located on or within a substrate 102 that forms at least part of a body of the contact lens. In an aspect, the substrate 102 is a hydrogel. Contact lenses disclosed herein can comprise any suitable material that can be employed to create cavities within the substrate. In an aspect, contact lenses disclosed herein include soft lenses made from one or more soft polymer materials including but not limited to, a hydrogel, a silicone based hydrogel, a polyacrlyamide, or a hydrophilic polymer. For example, in an aspect, contact lenses disclosed herein comprise of crosslinked hydrogels comprising hydrophilic monomers (e.g. N-Vinylpyrrolidone, 1-Ethenyl-2-pyrrolidone,N,N-dimethylacrylamide, 2-hydroxyethyl methacrylate, hydroxyethyl acrylate, methacrylic acid and acrylic acid), strengthening agents, ultraviolent light (UV) blockers, and tints. In another aspect, contact lenses disclosed herein comprise of silicone hydrogels (e.g. crosslinked hydrogels containing silicone macromers and monomers, as well as hydrophilic monomers that absorb water). In yet another aspect, contact lenses disclosed herein include hard lenses made from one or more rigid materials including but not limited to, a silicone polymer, polymethyl methacrylate, or rigid gas permeable materials.

In an embodiment, the substrate 102 of the tear collecting contact lens comprises a plurality of cavities that form an intricate network of canals and/or cells. According to this embodiment, the substrate can serve as a sponge and absorb tear fluid when worn on/in an eye. In other aspects, a tear fluid collecting contact lens described herein may include a single cavity, one or more isolated cavities with one or more openings at a surface of the contact lens, one or more isolated cavities without openings at a surface of the contact lens, or a combination of such various cavities.

Contact lenses disclosed herein are generally provided in a spherical shape that conforms to the shape of the eye. With reference to FIG. 1A, contact lenses disclosed herein include two primary surfaces, an inner surface 106 and an outer surface 104, both of which are spherical. The inner surface 106 is concave and is shown facing and resting on the surface of the eye 106 can conforming to the shape of the cornea. The outer surface 104 is convex. The contact lens has a thickness that spans in the horizontal direction between inner surface 106 and outer surface 104. Dashed line W indicates the direction of the width or depth of the lens. The diameter of the lens is indicated by dashed line D. The particular dimensions (including dimensions attributable to thickness, diameter, curvature, and etc.) of the subject contact lenses are not critical and may vary. Although contact lenses are depicted herein having a thicker/wider width (relative to the width of the lens at other areas) at the center point of the lens and tapering outwardly to a knifelike edge at the perimeter of the lens, such depiction is merely for exemplary purposes. For example, many corrective power lenses are thinner in the center of the lens then in the mid-periphery of the lens.

Cavities disposed within the contact lens substrate can have any suitable size and shape that facilitate collection of tear fluid without irritating the eye, without disrupting the functions of the eye, without disrupting the function of the contact lens, and without causing discomfort to the wearer. In an aspect, as seen in FIGS. 2A and 2B for example, the cavities 108 can be located at or near a perimeter of the contact lens so that cavities are not located in front of the optical region, (e.g. the pupil 110 and the iris 112) of the eye when the contact lens in worn in the eye. According to this aspect, a cavity provided within the substrate of a contact lens may have a length slightly less than the radius of the contact lens. However a cavity may be provided that has a length that ranges substantially the length or diameter of the substrate. In an aspect, a cavity provided within the substrate of a contact lens can have a depth that spans within the thickness of the substrate, including the entire thickness. For example, thickness of the substrate of a contact lens can be from about 20.0 µm to about 500 µm depending on type of lens and the distance from center point. According to this aspect, where the substrate has a thickness of about 5000 µm, a cavity can have a width or depth of about 500 µm or less. In another aspect, where the substrate has a thickness of about 150 µm, a cavity can have a width or depth of about 150 µm or less. In one embodiment, a cavity has a depth of at least 10 µm and still collect a substantial amount of tear fluid, regardless of the thickness of the substrate. In an embodiment, cavities provided within the subject tear collecting contact lenses are considered microcavities. The term microcavity as used herein includes cavities, channels, cells, or other cavity capable of collecting and storing tear fluid having a volumetric size less than the entire volume of the substrate in which it is located. In an aspect, the total volume of the contact lens substrate is about 25 to about 50 micro liters. With this in mind, in an aspect, a microcavity has a volume less than about 50% of the total volume of the substrate. In another aspect, a microcavity has a volume less than about 25% of the total volume of the substrate. In another aspect, a microcavity has a volume less than about 10% of the total volume of the substrate. In yet another aspect, a microcavity has a volume less than about 5% of the total volume of the substrate. In yet another aspect, a microcavity has a volume less than about 0.1% of the total volume of the substrate. Still in yet another aspect a microcavity has a volume less than about 0.01% of the total volume of the substrate.

Referring back to the drawings, FIG. 1A presents one example of a tear collecting contact lens 110 in accordance with disclosed aspects. Contact lens 110 comprises a substrate 102, such as a silicone hydrogel. The lens 110 comprises an inner surface 106 that faces and touches the eye 116 when inserted on/in the eye 116 and an outer surface 104 opposite the inner surface. Lens 110 comprises a plurality of cavities 108 that can fill with tear fluid over time when the lens 110 is worn or/in the eye 116. The cavities 108 of lens 110 are provided having a depth/length that spans the width of the substrate (e.g. substantially perpendicular to a surface of the lens). It should be appreciate that the number of cavities depicted (e.g. eight) and the proportional size of the cavities depicted is not limiting and is merely intended for exemplary purposes. For example, lens 110 can have any number N of cavities (where N is an integer) of varying size. The cavities 108 of lens 110 are located within the substrate 102 on the inner surface 106 of the lens. Further, the cavities 108 are disposed a radial distance away (e.g. about 2.0-6.0 mm) from the center of the lens so as not to cover the optical region of the lens (e.g. the region of the lens covering the pupil 112 and the iris 114). In an aspect, the cavities 108 of lens 110 include respective openings 118 at the interface between the substrate and the inner surface of the lens 106. According to this aspect, cavities 108 of lens 110 may receive tear fluid provided on or near the surface of the eye in the area between the contact lens 110 and the eye 116.

FIG. 1B presents another example of a tear collecting contact lens 120 in accordance with disclosed aspects. Contact lens 120 comprises a substrate 102, such as a silicone hydrogel. The lens 120 comprises an inner surface 106 that faces and touches the eye 116 when inserted on/in the eye 116 and an outer surface 104 opposite the inner surface. Lens 120 comprises a plurality of cavities 108 that can fill with tear fluid over time when the lens 120 is worn or/in the eye 116. The cavities 108 of lens 120 are provided having a depth/length that spans the width of the substrate (e.g. substantially perpendicular to a surface of the lens). It should be appreciate that the number of cavities depicted (e.g. eight) and the proportional size of the cavities depicted is not limiting and is merely intended for exemplary purposes. For example, lens 120 can have any number N of cavities (where N is an integer) of varying size. The cavities 108 of lens 120 are located within the substrate 102 on the outer surface 104 of the lens. Further, the cavities 108 are disposed a radial distance away (e.g. about 2.0-6.0 mm) from the center of the lens so as not to cover the optical region of the lens (e.g. the region of the lens covering the pupil 112 and the iris 114). In an aspect, the cavities 108 of lens 120 include respective openings 118 at the interface between the substrate and the outer surface of the lens 106. According to this aspect, cavities 108 of lens 120 may receive tear fluid provided on or near the outer surface 104 of the contact lens 120.

FIG. 1C presents one example of a tear collecting contact lens 130 in accordance with disclosed aspects. Contact lens 130 comprises a substrate 102, such as a silicone hydrogel. The lens 130 comprises an inner surface 106 that faces and touches the eye 116 when inserted on/in the eye 116, and an outer surface 104 opposite the inner surface. Lens 130 comprises a plurality of cavities 108 that can fill with tear fluid over time when the lens 130 is worn or/in the eye 116. The cavities 108 of lens 130 are provided having a depth/length that spans the width of the substrate (e.g. substantially perpendicular to a surface of the lens). It should be appreciate that the number of cavities depicted and the proportional size of the cavities depicted is not limiting and is merely intended for exemplary purposes. For example, lens 130 can have any number N of cavities (where N is an integer) of varying size. Further, the cavities 108 are disposed a radial distance away (e.g. about 2.0-6.0 mm) from the center of the lens so as not to cover the optical region of the lens (e.g. the region of the lens covering the pupil 112 and the iris 114). In an aspect, the cavities 108 of lens 130 include respective openings 118 at both the interface between the substrate and the inner surface of the lens 106 and the substrate and the outer surface of the lens. According to this aspect, cavities 108 of lens 130 may receive tear fluid provided on or near the surface of the eye in the area between the contact lens 110 and the eye 116 and tear fluid provide on the outer surface 104 of the lens.

FIG. 1D presents another example of a tear collecting contact lens 140 in accordance with disclosed aspects. Contact lens 140 comprises a substrate 102, such as a silicone hydrogel. The lens 140 comprises an inner surface 106 that faces and touches the eye 116 when inserted on/in the eye 116 and an outer surface 104 opposite the inner surface. Lens 140 comprises a plurality of cavities 108 that can fill with tear fluid over time when the lens 140 is worn or/in the eye 116. The cavities 108 of lens 140 are rod shaped and located within the substrate of the lens 102. It should be appreciate that the number of 108 cavities depicted and the proportional size of the cavities depicted is not limiting and is merely intended for exemplary purposes. For example, lens 140 can have any number N of cavities (where N is an integer) of varying size. Further, the cavities 108 are disposed a radial distance away (e.g. about 2.0-6.0 mm) from the center of the lens so as not to cover the optical region of the lens (e.g. the region of the lens covering the pupil 112 and the iris 114). In an aspect, the cavities 108 of lens 140 do not have openings at a surface of the lens.

In an aspect, the rod shaped cavities 108 of lens 140 can have one or more openings 118 within the substrate 102. For example, a rod shaped cavity may have a small hole through which tear fluid enters. In an embodiment, the substrate 102 of the lens 140 comprises a hydrophilic material that facilitates the passage of oxygen and tear fluid there through, creating a "wet" environment within the substrate 102 of lens 140. According to this embodiment, the "wet" environment of the substrate 102 of lens 140 facilitates the process (e.g. capillary action and/or osmosis) by which the rod shaped cavities fill with tear fluid.

FIG. 1E presents another example of a tear collecting contact lens 150 in accordance with disclosed aspects. Contact lens 150 comprises a substrate 102, such as a silicone hydrogel. The lens 150 comprises an inner surface 106 that faces and touches the eye 116 when inserted on/in the eye 116 and an outer surface 104 opposite the inner surface. Lens 150 comprises a plurality of cavities 108 that can fill with tear fluid over time when the lens 150 is worn or/in the eye 116. The cavities 108 of lens 150 are provided having a depth/length that spans the length of the substrate (e.g. substantially parallel to a surface of the lens). It should be appreciate that the number of cavities depicted (e.g. two) and the proportional size of the cavities depicted is not limiting and is merely intended for exemplary purposes. For example, lens 150 can have any number N of cavities (where N is an integer) of varying size. The cavities 108 of lens 150 are located within the substrate 102 and disposed a radial distance away (e.g. about 2.0-6.0 mm) from the center of the lens so as not to cover the optical region of the lens (e.g. the region of the lens covering the pupil 112 and the iris 114). In an aspect, the cavities 108 of lens 150 include respective openings 118 at the perimeter/outermost edge 122 of the substrate.

With reference to FIG. 2A, presented is an example of a tear collecting contact lens 210 in accordance with disclosed aspects. Lens 210 presents a top planar view of a lens 210 as worn over/in an eye. In an aspect, lenses 110, 120, 130 and 140 can have top planar configurations same or similar to that depicted of lens 210. In particular, the cross-section of lens 210 taken along axis Y can resemble the cross-sections of lenses 110, 120, 130 and 140, where the cavities 108 of lens 210 and similarly lenses 110, 120, 130 and 140, are provided having a depth/length that spans the width of the substrate (e.g. substantially perpendicular to a surface of the lens). It should be appreciate that the number of cavities 108 depicted and the proportional size of the cavities depicted is not limiting and is merely intended for exemplary purposes. For example, lens 210 can have any number N of cavities (where N is an integer) of varying size. The cavities 108 of lens 210 are located within the substrate 102 and are disposed a radial distance away (e.g. about 2.0-6.0 mm) from the center of the lens so as not to cover the optical region of the lens (e.g. the region of the lens covering the pupil 112 and the iris 114).

With reference to FIG. 2B, presented is another example of a tear collecting contact lens 220 in accordance with disclosed aspects. Lens 220 presents another top planar view of a lens 220 as worn over/in an eye. In an aspect, lens 220 is the top planar configuration of lens 150. In particular, the cross-section of lens 220 taken along axis Y can resemble the cross-section of lens 150, where the cavities 108 of lens 220 and similarly lens 150, are provided having a depth/length that spans a length of the substrate (e.g. substantially parallel to a surface of the lens). It should be appreciate that number of cavities 108 depicted and proportional size of the cavities depicted (e.g. eight) is not limiting and is merely intended for exemplary purposes. For example, lens 220 can have any number N of cavities (where N is an integer) of varying size. The cavities 108 of lens 220 are located within the substrate 102 and are disposed a radial distance away (e.g. about 2.0-6.0 mm) from the center of the lens so as not to cover the optical region of the lens (e.g. the region of the lens covering the pupil 112 and the iris 114). In an aspect, cavities 108 have respective openings 118 at an outer edge/perimeter 122 of the lens 220.

Referring now to FIGS. 3A-3F, presented are exemplary embodiments of a contact lenses that facilitate collection and analysis of one or more biological features associated with a wearer of the contact lens. In an aspect, the biological features are located within tear fluid generated by the wearer of the contact lens. Further, in some aspects, the tear fluid can be collected in one or more cavities provided on or within the substrate 102 of the lens as discussed above.

With reference first to FIG. 3A, presented is an example of a contact lens 320 comprising one or more receptors 302 disposed on and within the substrate 102. The one or more receptors are configured to bind to a known ligand. As used herein, the term receptor includes a biological or chemical component having a binding site for a known ligand. A receptor can include but is not limited a biomolecule (including proteins, peptides, polysaccharides, lipids, hormones and nucleic acids as well as small molecules such as primary metabolites, secondary metabolites, and natural products), an antibody, an antibody linked with an enzyme, an antigen, or a synthetic molecule. The term ligand refers to a molecule having a known binding affinity for a known receptor. By definition, the ligand is the molecule which binding properties are to be analyzed. A ligand can include but is not limited to, a chemical, (e.g. like a reporter fluorophore or other small molecule), a biomolecule, a complex organism (e.g. like human pathogens of viral or bacterial origin) a pharmaceutical drug, a toxin, and antigens or an antibody. Ligands can also include airborne molecules and chemicals including but not limited to pollutants, allergens, viruses, or bacteria. In one or more aspects, receptors are employed that bind to known ligands that serve as biomarkers. As used herein, the term biomarker refers to a biological molecule or substance that can be used to indicate a biological state. Biomarkers are characteristic in that they can be objectively measured and evaluated as indicators of normal biological processes, pathogenic processes, or pharmacologic responses to a therapeutic intervention.

In some aspects, a molecule may serve as a ligand in one use context and a receptor in another use context. For example, in an aspect, an antibody may serve as a receptor for detecting the presence of a known antigen in tear fluid. However, in another aspect, the antigen can serve as a receptor for detecting the presence of a known antibody in tear fluid. For example, the presence of a known antibody may indicate signs of a particular infection. Nevertheless, as disclosed herein, receptors are provided on and/or within disclosed contact lenses during the manufacturing process of the contact lenses while ligands are introduced to the lens following manufacture. In particular, receptors 302 are provided on and/or within contact lenses for the purpose of detecting known ligands in the environment external to the human body and/or known ligands present within the human body, (e.g. known ligands surfacing within the eye cavity, on the eye, and/or within tear fluid).

Contact lens 320 comprises a substrate 102, such as a silicone hydrogel. The lens 320 comprises an inner surface 106 that faces and touches the eye 116 when inserted on/in the eye 116, and an outer surface 104 opposite the inner surface. FIG. 3D is a magnified view of lens 320 at area 304, represented by the dashed box. As seen in FIG. 3D, the substrate 102 comprises a plurality of receptors 302 provided at various locations on and within the substrate. In an aspect, receptors 302 are provided fixed to the outer surface 104 of the substrate and external from the substrate. According to this aspect, the receptors can be configured to bind to a known ligand present in an environment external from an eye in which the contact lens is being worn. For example, the known ligand can include a pollutant or an allergen present in the environment.

In another aspect, the receptors 302 are provided fixed to the outer surface 104 of the substrate and within the substrate. In yet another aspect, receptors 302 are provided fixed to the inner surface 106 of the substrate and external from the substrate. In yet another aspect, the receptors 302 are provided fixed to the inner surface 106 of the substrate and within the substrate. Still in yet another aspect, receptors 302 can be dispersed within the substrate 102. It should be appreciated that lens 320 may be modified to include receptors at a single location. For example, a contact lens may only include receptors 302 within the substrate 102 or may only include receptors fixed to an external surface of the substrate. Further, although lens 320 is presented with a single type of receptor, (e.g. the receptor having the Y shape), it should be appreciated that two or more different types of receptors may be provided on and/or within a substrate. In particular, a contact lens disclosed herein may include any number N of receptors and any number M of different types of receptors, where N and M are integers.

FIG. 3B presents an example contact lens 330 comprising one or more receptors 302 disposed within one or more cavities 306 located within the substrate 102. FIG. 3E is a magnified view of lens 330 at area 308, represented by the dashed box. As seen in FIG. 3E, the substrate 102 comprises a plurality of receptors 302 provided within cavities 306 located within the substrate 102. In an aspect, the cavities 106 are configured to collect and store tear fluid over time when the lens 330 is worn in an eye. The tear fluid may contain ligands that bind to the receptors 302 located within the cavities 306.

In particular, magnified area 308 presents one cavity having an opening 310 at the outer surface 104 of the lens and another cavity having an opening 310 at the inner surface 106 of the lens. According to this aspect, the cavity having the opening 310 at the outer surface 104 can include receptors that are configured to bind to a known ligand present in an environment external from an eye in which the contact lens is being worn. For example, the known ligand can include a pollutant or an allergen present in the environment. On the other hand the cavity having the opening 310 at the inner surface 106 of the substrate can include receptors that are configured to bind to a known biological ligand surfacing from the body of the wearer of the lens. For example, the known ligand can include a monosaccharide. It should be appreciated that any cavity design and configuration, such as those discussed with reference to FIGS. 1A-1E and 2A-2B, can be provided with receptors therein.

In an aspect, cavities located within the substrate 102 can include different types of receptors. For example, the magnified area of lens 330 depicts a first receptor (having the U shape) disposed with a first cavity, wherein the first cavity is disposed within the substrate and a second receptor (having the Y shape) disposed within a second cavity, wherein the second cavity is disposed within the substrate. The first receptor is configured to bind to a first known ligand and the second receptor is configured to bind to a second known ligand different from the first known ligand. Further, a single cavity may include different types of receptors (not shown). In an aspect, the receptors can be dispersed or float within a cavity 306. In yet another aspect, the receptors 302 can be fixed to a surface of the cavity and within the cavity.

FIG. 3C presents an example contact lens 340 comprising one or more receptors 302 disposed within one or more cavities 306 located within the substrate 102. FIG. 3F is a magnified view of lens 340 at area 314, represented by the dashed box. As seen in FIG. 3F, the substrate 102 comprises a plurality of receptors 302 provided within cavities 306 located within the substrate 102. In an aspect, the cavities 106 are configured to collect and store tear fluid over time when the lens 330 is worn in an eye. The tear fluid may contain ligands that bind to the receptors 302 located within the cavities 306. The cavities 306 of lens 340 include rod shaped cavities that do not have openings at a surface of the substrate. In an aspect, the rod shaped cavities can have one or more small openings 310 that facilitate the influx of tear fluid. In an aspect, separate cavities may have different receptor types provided therein to facilitate the testing of different biological states associated with the different ligands that respectively bind to the different receptors. For example, lens 340 includes a first cavity having a U type receptor, a second cavity having a Y type receptor, and a third cavity having an F type receptor. It should be appreciated that each of the different receptor types are tailored to have a binding affinity for different types of ligands.

With reference now to FIGS. 4A-4C, the magnified regions 304, 308, and 314 of contact lenses 320, 330, and 340 respectively, are reproduced in FIGS. 4A, 4B, and 4C respectively. FIGS. 4A, 4B, and 4C present example contact lenses 320, 330, and 340 following the wearing of the respective contact lenses in an eye for a period of time. In FIGS. 4A-4C, for demonstrative purposes, the wearer of the contact lenses 320, 330, and 340 and/or the environment in which the wearer of the contact lens is located, produces two types of ligands, ligand Y and ligand U. Ligand Y is configured to bind to receptor Y and ligand U is configured to bind to receptor U.

As seen in FIG. 4A, some of the Y receptors are bound to their reciprocal ligands. Further, although ligands U are present within or near the contact lens, the lens does not include any U receptors. Accordingly, the U ligands remain unbound. As seen in FIG. 4B, some of the Y receptors are bound to their reciprocal ligands within the cavity having an opening at the outer surface 104 of the substrate. In an aspect, the Y ligands may be associated with an external allergen present in the environment. Also, some of the U receptors are bound to their reciprocal ligands within the cavity having an opening at the inner surface 106 of the substrate. In an aspect, the U ligands may be associated with a protein generated by the body of the wearer of the contact lens and be provided in tear fluid collected in the cavity 306. As seen in FIG. 4C, some of the Y receptors are bound to their reciprocal ligands within the rod shaped cavities having Y receptors. Similarly, some of the U receptors are bound to their reciprocal ligands within the rod shaped cavity having U receptors. However, the F receptors do not have any bound ligands as the wearer of the lens and the environment do not produce the appropriate ligand.

Figure 6:
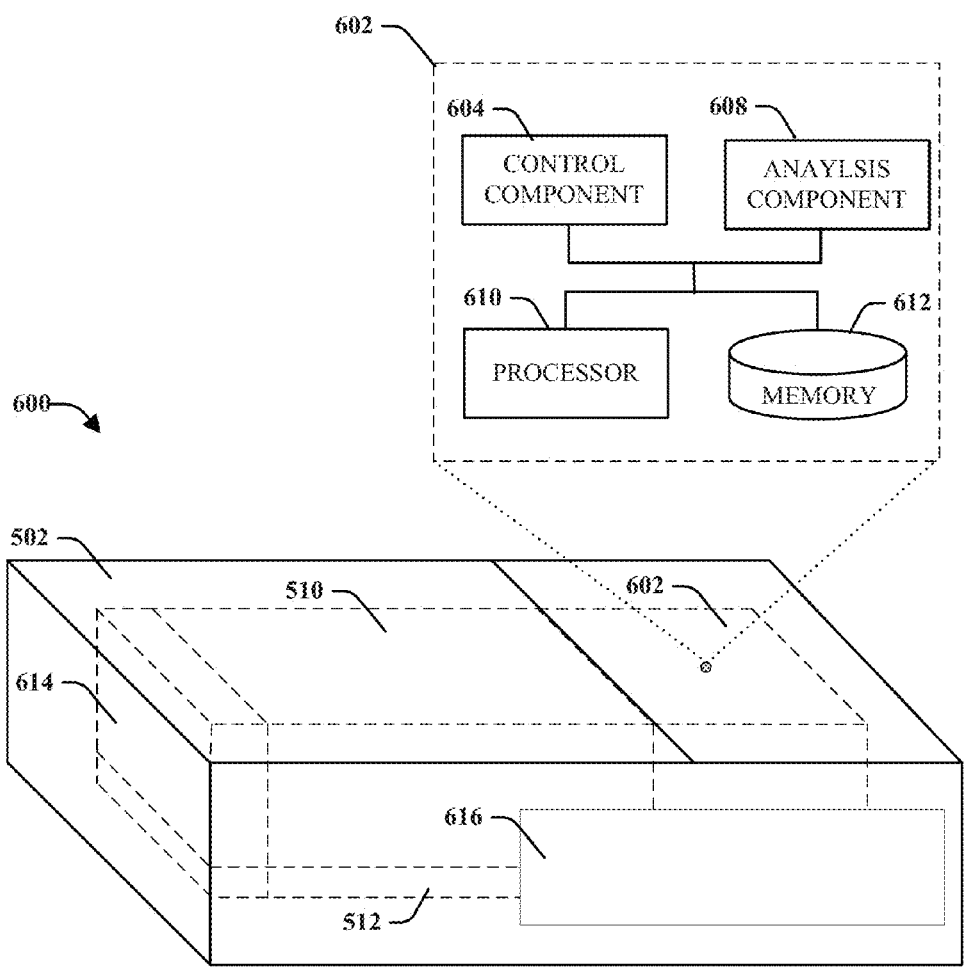
FIG. 6 is another illustration of a block diagram of an exemplary, non-limiting apparatus that facilitates testing of contact lenses.
Figure 7:
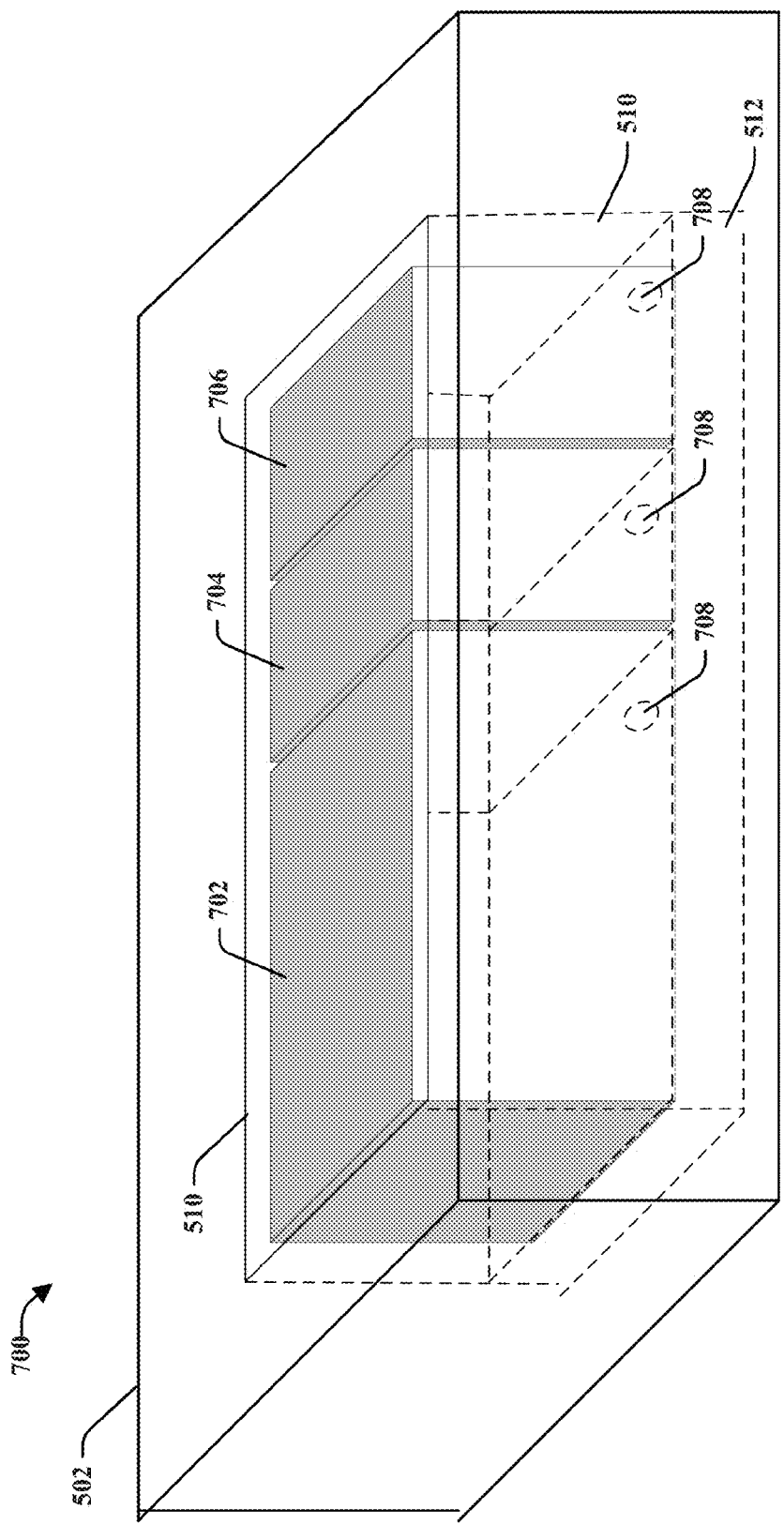
FIG. 7 is another illustration of a block diagram of an exemplary, non-limiting apparatus that facilitates testing of contact lenses.

FIGS. 5-7 depict testing apparatuses/devices that are configured to test worn contact lenses for various biomarkers or other environmental substances present on and/or within the worn lenses. In turn, an individual and/or the apparatus itself, may determine one or more biological states of the wearer of a tested contact lens or the environment based on the identified biomarkers or environmental substances respectively. In an aspect, the apparatuses can test substantially any available worn contact lens for biomarkers. In another aspect, the apparatuses can test tear collecting contact lenses as disclosed herein. In particular, the subject tear collecting contact lenses can be provided to a disclosed testing apparatus for testing of the tear fluid stored therein. Still in yet another aspect, the disclosed testing apparatuses are configured to perform one or more ligand binding assays to identify a type and/or quantity of known ligand attached to a receptor provided on and/or within a worn contact lens. In various embodiments, one or more functions and features of an example testing device disclosed herein can be combined with another example testing device disclosed herein.

With reference now to FIG. 5, presented is an embodiment of a an example contact lens testing apparatus 500 that tests worn contact lenses for one or more biomarkers or environmental substances present on and/or within the worn contact lenses. Testing apparatus 500 includes at least a housing 502 and a testing compartment 510. The housing is configured to hold one or more contact lenses 506 and the testing compartment 510 is configured to apply one or more tests on contact lenses placed in the housing 502. As shown in FIG. 5, the testing compartment 510 is located within the housing 502 and the contact lenses 506 are placed within the testing compartment for testing thereof. In an aspect, the testing compartment 510 can include a lid 504 to enclose and seal off the testing compartment 510. The housing 502 may also include a lid (not shown), to enclose the housing. In an aspect, in addition to the testing compartment 510, the housing may hold additional components that can be used to facilitate testing of contact lenses (not shown). For example, the housing may hold components of a contact lens testing kit, such as reagents, buffer solutions, rinsing solutions, and other tools.

In an embodiment, one or more reagents are provided within the testing compartment 510 that facilitate a chemical reaction in response to the existence of a predetermined substance, such as a biomarker or an environmental chemical, disposed on or within a contact lens placed therein. In an aspect, the one or more reagents are provided within the testing compartment 510 as a liquid/buffer solution. For example, dotted line 508 of FIG. 5 represents a water/liquid line, below which the contact lenses 506 are located. In some aspects, the housing 502 may hold one or more reagent solutions in small separate containers so that a user can apply the reagent to worn contact lens within the testing compartment 510. For example, testing device 502 may require a user to apply a first reagent, wait five minutes, and then apply a second reagent.

The chemical reaction can produce a known result related to state information of an individual from which the biomarker was generated. For example, the chemical reaction could result in appearance of a color or production of a product (such as a precipitate or an odor). Such result can be indicative of state information of an individual from which the biomarker was generated. In an aspect, in order to relate chemical test results to state information, the testing device 500 may be provided with simple instructions which inform a user how to read test results and relate the test results to state information.

In an example, a user may wear contact lenses throughout the day and take the lenses out prior to going to sleep. The user can place the worn lenses into the testing compartment 510 of a testing device such as device 500 and leave the lenses in the testing compartment for a period of time necessary for a preconfigured chemical reaction to occur. While the contact lenses are within the testing compartment 510, the reagent in the testing compartment 510 may react with a biomarker located on or within the worn contact lenses and produce a red color. For example, a liquid solution in which the contact lenses are placed, provided in the testing compartment 510, may turn red. The red color may further be indicative of high blood sugar. Accordingly, the user can become informed that he has high blood sugar merely by testing his worn contact lenses with testing apparatus 500.

It should be appreciated that testing device 500 can be configured to perform a variety of tests for different biomarkers and substances depending on the reagents provided therewith. Accordingly, depending on the biomarkers or substances which the testing device is designed to test for, different information about the state of the wearer of the contact lenses and/or the environment can be discerned. In an aspect, state information about the wearer of the contact lens can include but is not limited to: glucose level, alcohol level, histamine level, urea level, lactate level or cholesterol level of the individual. In another aspect, state information about the wearer of the contact lens can include but is not limited to: sodium ion level, potassium ion level, calcium ion level or magnesium ion level of the wearer of the contact lens.

In an aspect, the testing compartment 108 can apply multiple tests to a single contact lens. For example, the testing compartment 510 may include multiple sub-testing compartments, each comprising a different regent. According to this aspect, a user can place a worn contact lens in each one of the different sub-testing compartments to test for a different substance. In another aspect, two or more reagents may be provided together in a single compartment of the testing compartment 510, each of which reacts with different molecules. In one embodiment, the testing compartment 510 comprises at least two compartments 514 and 516, each comprising a different reagent configured to react with a different substance and produce different results. According to this aspect, a user can place a left contact lens in one compartment and a right contact lens in another compartment to test for two different biomarkers, and associated biological states, at the same time.

In an embodiment, testing apparatus 500 receives and tests tear collecting contact lenses, such as those disclosed with reference to FIGS. 1A-3F. According to this embodiment, the biomarkers or substances which the testing device tests for can be located in the tear fluid collected in the one or more cavities of the contact lenses. In an aspect, a chemical compound can be provided within the testing compartment 510 to facilitate extracting tear fluid from a cavity in which it is held. For example, a chemical can be provided within the testing compartment 508 that dissolves walls of the cavity, and/or that dissolves part or all of the substrate of the contact lens having the cavity, when the lens is placed therein. The dissolving chemical can be selected such that the chemical does not affect the testing process and function of the testing apparatus 500. For example, the dissolving chemical can be selected such that the chemical does not affect the functions of a reagent provided in the testing compartment and such that the chemical does not interfere with the structure of the molecules the reagent is configured to react with.

In an aspect, the testing apparatus 500 can include an extraction component 512 that extracts tear fluid from one or more cavities disposed within a contact lens placed in the housing 502. The extraction component 512 can employ any suitable mechanical means to facilitate extracting tear fluid from cavities located within a substrate of a contact lens placed within the testing compartment 510. In an aspect, the extraction component 512 can employ compression means whereby the extraction component 512 creates pressure within the testing compartment 510 to force the tear fluid out of the cavities. For example the extraction component 510 may create pressure within testing compartment via air or mechanical force that results in "poping" of the cavities. In another aspect, the extraction component 512 can apply shearing forces and/or shearing devices to shred the contact lens and the cavities within. In some aspects, the extraction component 512 can separate the tear fluid from other constituents of the contact lens in which the tear fluid is located.

FIG. 6 presents another embodiment of a contact lens testing apparatus 600 that tests worn contact lenses for one or more biomarkers or environmental substances present on and/or within the worn contact lenses. Apparatus 600 can include same or similar features of contact lens 500 with the addition of various machine based components and functions. In particular, in an aspect, in addition to performing testing of contact lenses, apparatus 600 can perform machine based analysis of tests results. For example, the apparatus 600 may determine biological states of the wearer of the tested contact lens and/or environmental factors based on test results. Further, apparatus 600 can conduct machine based tests on worn contact lenses, such as spectroscopic analysis.

In an embodiment, aspects of apparatuses and processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Apparatus 600 can include memory 612 for storing computer executable components and instructions. A processor 610 can facilitate operation of the computer executable components and instructions by apparatus 600.

Testing apparatus 600 can include a housing 502 that holds one or more contact lenses, a testing compartment 510 in which worn contact lenses can be placed for the performance of testing thereof, and extraction component 512. Testing apparatus 600 can further include operating component 602 that includes one or more machine executable components. In an aspect, operating component 602 includes the processor 610 and memory 612. Operating component 602 can further include control component 604 and analysis component 608. In addition, testing apparatus 600 can include a display screen 616 (e.g. an LCD display and/or an interactive touch screen display), and a hardware component 614.

Control component 604 is configured to control the operations of testing apparatus 600. In an aspect testing apparatus 600 can be configured to perform chemical testing of worn contact lenses. In another aspect, testing apparatus 600 can be configured to perform spectroscopic analysis of worn contact lenses. Chemical testing of worn contact lenses can include the application of one or more reagents to a worn contact lens that produce a chemical reaction with one or more substances on or within the worn contact lens. The chemical reaction can further produce a known result that can be employed to identify and/or quantify a substance (e.g. a biomarker or environmental substance) on the worn contact lens. For example, a reagent may be applied to a worn contact lens that interacts with a known biomarker to produce a known color or product.

Spectroscopic analysis measures radiated energy of molecules as a function of wavelength or frequency. In an aspect, testing apparatus 600 performs spectroscopic analysis on tear fluid provided within one or more cavities of a tear collecting contact lens as described herein. Testing apparatus 600 can be configured to perform a variety of spectroscopic analysis, including but not limited to: atomic absorption spectroscopy, attenuated total reflectance spectroscopy, electron paramagnetic spectroscopy, electron spectroscopy, Fourier transform spectroscopy, gamma-ray spectroscopy, infrared spectroscopy, laser spectroscopy, mass spectrometry multiplex or frequency-modulated spectroscopy, Raman spectroscopy, and x-ray spectroscopy.

Control component 604 controls the performance of the testing carried out in testing compartment 510. In an aspect, a user may simply be required to place a worn contact lens into testing apparatus 600, select a test to be performed on the worn contact lens via a menu presented on display screen 616, and in response to selection, the test may be performed at the control of control component 604. Further, analytical results of the test performed can be provided to the user, such as via the display screen. In other aspects, the control component 604 may prompt a user (e.g. via display screen) to carry out one or more processing steps in association with testing. For example, the control component 604 may require a user to remove a contact lens from a first sub-testing compartment and transfer the contact lens into a second sub-testing compartment of testing compartment 510.

Analysis component 608 analyzes one or more biomarkers or other substances disposed on and/or within one or more contact lenses placed within testing compartment 510 to determine information associated with the biomarkers or other substances. In particular, analysis component 608 analyzes test results of a test performed on a worn contact lens by testing compartment 510 to determine state information associated a state of an individual from which the biomarkers were generated or information about the environment. For example, analysis component 608 can analyze results of a chemical test or a spectroscopic test using information associating known results of such tests to various state information or environmental information stored in memory 612. In an aspect, state information about the wearer of the contact lens that may be determined by analysis component 608 can include but is not limited to: glucose level, alcohol level, histamine level, urea level, lactate level or cholesterol level of the individual. In another aspect, state information about the wearer of the contact lens that may be determined by the analysis component 608 can include but is not limited to: sodium ion level, potassium ion level, calcium ion level or magnesium ion level of the wearer of the contact lens. Information that may be determined about the environment by analysis component 108 can include for example, pollution levels, pollen levels, or information about airborne viruses.

Hardware compartment 614 can include necessary hardware components for running machine based testing and analysis of worn contact lenses including the necessary circuitry, power components (e.g. battery), other hardware component to facilitate testing. For example, the hardware component 614 can include an energy source for a spectrometer, a spectrophotometer or an interferometer. In addition, the hardware component 614 may include mechanical components that facilitate operation of extraction component 512. In particular, extraction component 512 may extract tear fluid from cavities of contact lenses placed in testing compartment 510 via a variety of mechanical means (e.g. using shearing devices, pressure generating devices, centrifuge devices, and etc.). Hardware component 614 may supply the machine driven mechanical means that facilitate extraction of tear fluid from cavities of contact lenses. For example, in an aspect, the extraction component 512 may shred a contact lens to extract the tear fluid from the one or more cavities therein prior to the performance of spectroscopic analysis of the tear fluid by testing compartment 510.

FIG. 7 presents another embodiment of an example contact lens testing apparatus 700 that tests worn contact lenses for one or more biomarkers or environmental substances present on and/or within the worn contact lenses. Apparatus 700 can include same or similar features of contact lens 600 with the addition of various components that facilitate performance of a ligand binding assay in association with a contact lens having receptors located on or within the contact lens that are configured to bind to a predetermined ligand (e.g. contact lenses 320, 330, 340 and the like). Example uses and testing procedures facilitated by apparatus 700 are further described with reference to FIGS. 8 and 9.

Testing apparatus 700 includes at least a housing 502 that holds one or more contact lenses. Testing apparatus further includes a testing compartment 510 disposed within the housing that facilitates determining presence of one or more biomarkers or other substances bound to one or more receptors disposed on or within a contact lens placed within the testing compartment 510. Identification of certain biomarkers or substances can further be used to determine state information associated with a state of an individual from which the biomarkers were generated and/or state information associated with the environment from which the other substances were generated. In an aspect, the one or more receptors are disposed in one or more cavities located within a body of the contact lens, and the one or more biomarkers bound to the one or more receptors are located in tear fluid that is held within the one or more cavities.

In some aspects, testing apparatus 700 can include an extraction component 512 that can extract the tear fluid from the one or more cavities without disrupting bonds between the one or more biomarkers and the one or more receptors. For example, the extraction component 512 may employ any suitable mechanical means (e.g. shredding, pressurization, centrifugal forces, and etc.) to separate tear fluid, unbound receptors, bound receptors, unbound ligands, and/or other substances, from one another to facilitate determining presence (and potentially quantification) of one or more biomarkers or other substances on or within a worn contact lens. In an aspect, the extraction component 512 can drain the testing compartment 510 via one or more drain holes 708 provided at the floor of the testing compartment. Drainage testing compartment 510 can be used to separate tear fluid, unbound receptors, bound receptors, unbound ligands, contact lens substrate material, and/or other substances, from one another.

As used herein, the term ligand binding assays refers to an assay, or an analytic procedure, whose procedure or method relies on the binding of ligand molecules to receptors and measures the binding activity of a biological or chemical component to another biological or chemical component. Ligand binding assays can be used by testing apparatus 700 to detect the presence and/or extent of ligand-receptor complexes formed on or within a worn contact lens placed within testing compartment 510. In an aspect, detection of ligand-receptor complexes is determined electrochemically. In another aspect, detection of ligand-receptor complexes is determined via a fluorescence method.

In one or more embodiments, contact lenses are configured with one or more receptors thereon and/or therein that are designed to detect a target ligand known to bind to the one or more receptors (e.g. contact lenses 320, 330, 340 and the like). The receptors and/or ligands can include biological components and/or chemical components. When such contact lenses are placed within the testing compartment 510 following wear the contact lenses, testing apparatus 700 facilitates determining whether the target ligand is bound to the one or more receptors via a ligand binding assay.

Testing apparatus 700 can be configured to perform a variety of ligand bonding assays. In particular, there are numerous types of ligand binding assays, both radioactive and non-radioactive, that may be employed by testing apparatus 700. As such, ligand binding assays are superset of radio-binding assays, which are the conceptual inverse of radio-immunoassays (RIA). Some types of ligand binding assays called "mix-and-measure," assays may be employed by testing apparatus 700 that do not require separation of bound from free ligand. In some aspects, a buffer solution may be provided within testing compartment 510 to facilitate liquid phase ligand binding assays. In other aspects, a worn contact lens can have previously immobilized receptors integrated thereon and/or therein can be used to perform a solid phase ligand binding assay. In an aspect, the ligand binding assay performed by testing apparatus 700 includes an enzyme-linked immunosorbent assay (ELISA). Performance of an ELISA involves at least one antibody with specificity for a particular antigen. Example ELISA based testing of contact lenses is described supra with respect to FIGS. 8 and 9.

As seen in FIG. 7, testing compartment 510 can include two or more sub-testing compartments 702, 704, and 706 that facilitate performance of a ligand bonding assay on a worn contact lens having receptors thereon and/or therein. In an aspect, testing compartment 510 can include a rinsing compartment 702, and one or more detection compartments 704 and 706 comprising detector molecules configured to facilitate detecting ligand/receptor complexes formed on and/or within a worn contact lens. It should be appreciated that in some aspects, detector molecules can be applied to contact lenses while the contact lens retains its form. In other aspects, detector molecules can be applied to a contact lens that has been shredded or dissolved. Still in other aspects, detector molecules may be applied to tear fluid extracted from a contact lens, the tear fluid having ligand/receptor complexes therein. In an aspect, rinsing compartment 702 can include a rinsing solution that removes at least one of unbound ligands (e.g. unbound biomarkers or other target substances) or unbound receptors from a worn contact lens when the contact lens is provided therein. The rinsing solution can be selected such that it does not bond between ligand/receptor complexes. For example, the rinsing solution may include a mild detergent mixed with water.

Detector molecules can be provided within a detection compartment 704 and/or 706 within a buffer solution. The detector molecules are configured to bind to at least one of, ligand/receptor complexes formed on and/or within a worn contact lens, ligand/receptor complexes provided in tear fluid from one or more cavities of the worn contact lens, or ligand/receptor complexes otherwise extracted from the contact lens, when the worn contact lens is placed within a detection compartment 704 and/or 706 having the detector molecules therein. In an aspect, the detector molecules are configured to bind to the one or more receptors on or within a worn contact lens having one or more biomarkers bound to the one or more receptors. The detector molecules can further can produce a signal in response to binding, such as the appearance of a color. For example, the detector molecules may include a substrate configured to bind to an enzyme covalently linked to the one or more receptors having the one or more biomarkers bound thereto. Upon binding of the substrate to the enzyme a color may be emitted.

In another aspect, the detector molecules may be configured to bind to the one or more ligands (e.g. biomarkers or other substances) bound to the one more receptors on and/or within a contact lens and produce a signal (e.g. the appearance of a color) in response to binding. According to this aspect, the detector molecules can include first detector molecules and second detector molecules. The first detector molecules can comprise a detector antibody covalently linked to an enzyme, the detector antibody configured to bind to the one or ligands bound to the one or more receptors. The second detector molecules can comprise a substrate configured to bind to the enzyme to produce the signal. According to this aspect, the first detector molecules may be provided within a first detection compartment 704, and the second detector molecules may be provided in a second detection compartment 706.

In an embodiment, a user of apparatus 700 or the apparatus itself (e.g. via an analysis component 608) may analyze results of ligand binding assays performed by apparatus 700 to determine state information associated with a wearer of a tested contact lens and/or state information associated with the environment in which the wearer of the tested contact lens was located. In an aspect, state information about the wearer of the tested contact lens can include but is not limited to: glucose level, alcohol level, histamine level, urea level, lactate level or cholesterol level of the individual. In another aspect, state information about the wearer of the tested contact lens can include but is not limited to: sodium ion level, potassium ion level, calcium ion level or magnesium ion level of the wearer of the contact lens. Further, information that may be determined about the environment can include for example, pollution levels, airborne allergens, pollen levels, or information about airborne viruses.

Figure 8:
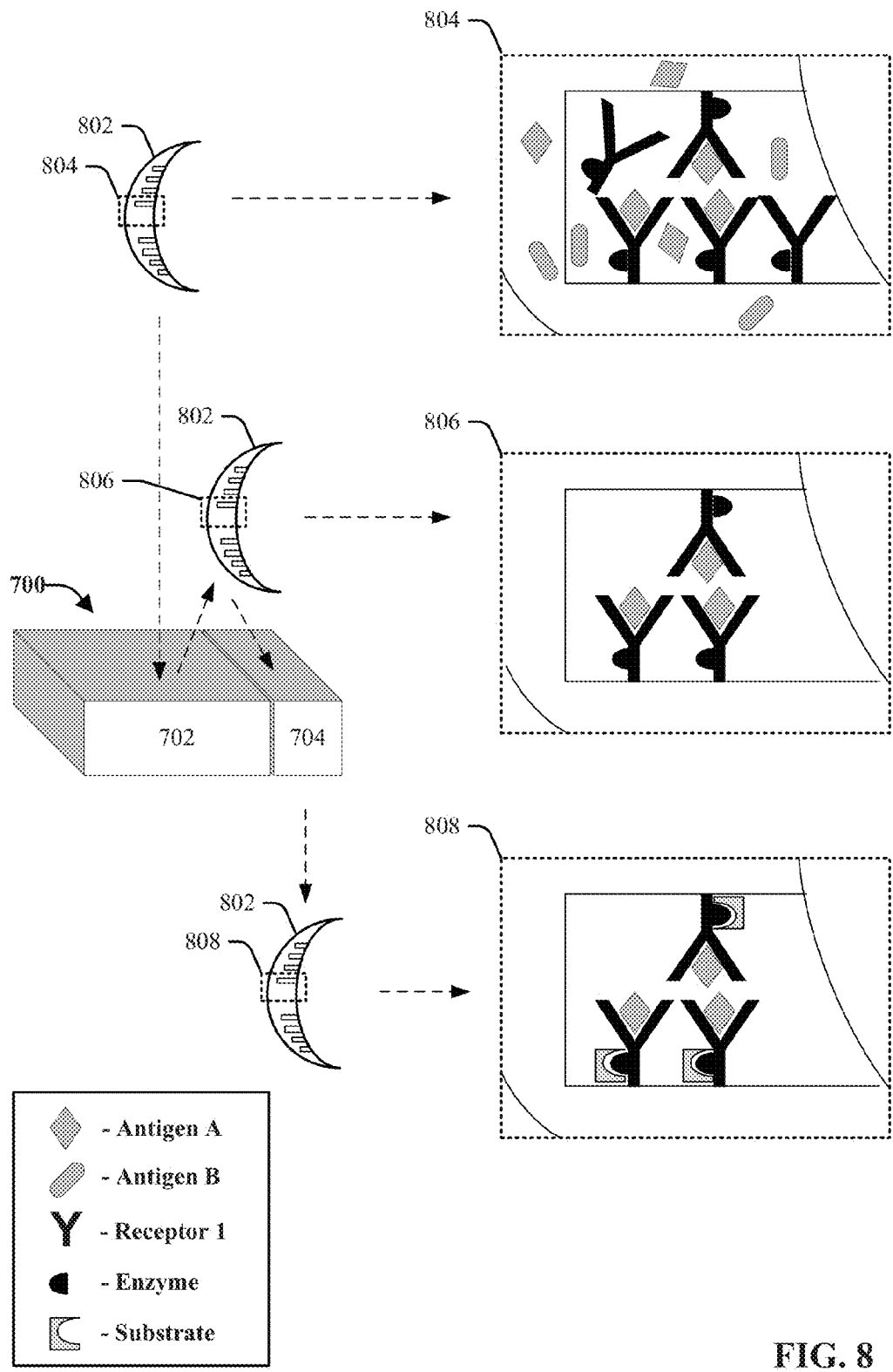
FIG. 8 presents an flow diagram of an exemplary application of a testing apparatus for testing of a contact lens having receptors for binding to a known ligand.

Referring now to FIG. 8, presented is an example application of testing apparatus 700 in accordance with an embodiment. FIG. 8 depicts an ELISA based testing of a worn contact lens 802. The testing performed in FIG. 8 involves a testing apparatus 700 having at least a rinsing compartment 702 and a single detector compartment 704 having detector molecules therein. Initially, a worn contact lens 802 is removed from an eye by a user and placed into the rinsing compartment 702. In this example, the contact lens 802 is a tear collecting contact lens having Y receptors provided within one or more of the tear collecting cavities. In an aspect, the Y receptors are antibodies. The Y receptors are further conjugated with an enzyme. Box 804 depicts a magnified view of area 804 of the worn contact lens prior to placing the worn contact lens into the rinsing compartment 702. As seen in box 804, some of the Y receptors are bound to their target ligand, antigen A. Further, some of the Y receptors remain unbound and some unbound antigen A and antigen B (for which the contact lens does not have a receptor), remains.

Box 806 depicts a magnified view of area 806 of the worn contact lens following rinsing of the contact lens 802 in rinsing compartment 702. As seen in box 806, the unbound Y receptors and unbound antigen A and B are washed away or removed from the contact lens and only the ligand/receptor complexes remain. The washed lens is then placed into detector compartment 704. Detector compartment includes detector molecules. In this example, the detector molecules are substrates that are configured to bind to enzymes covalently linked to the Y receptors and produce a signal. Accordingly, when contact lens 802 is provided within detection compartment 704, the substrates bind to the enzymes, as seen in the enlarged picture of area 808 of the contact lens at box 808. In an aspect, the signal produced in response to binding of the substrates to the enzymes is a visible color that may be observed by a user and or that may be measured using spectroscopic analysis.

Figure 9A:
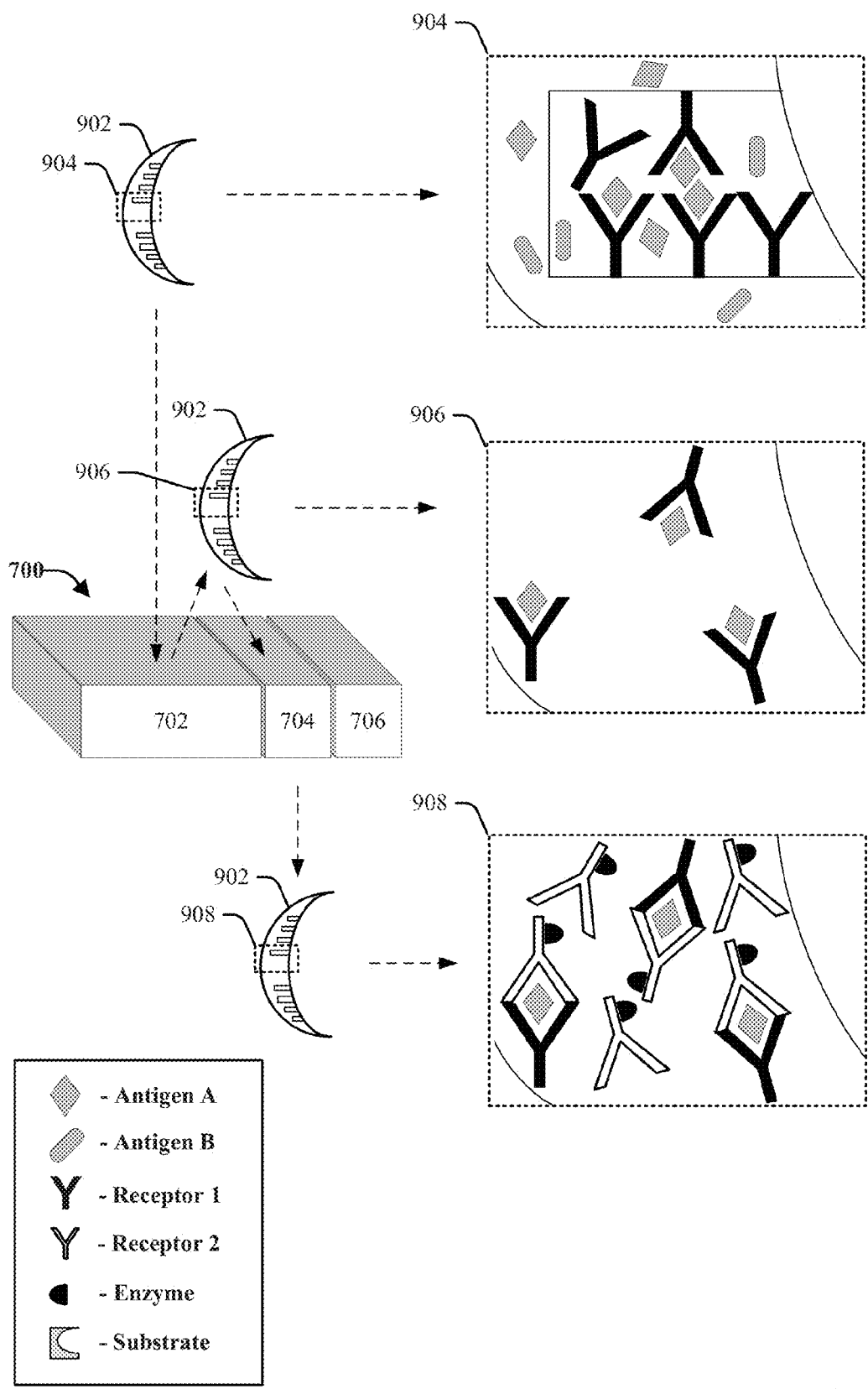
FIG. 9A and FIG. 9B present a flow diagram of an exemplary application of a testing apparatus for testing of a contact lens having receptors for binding to a known ligand.
Figure 9B:
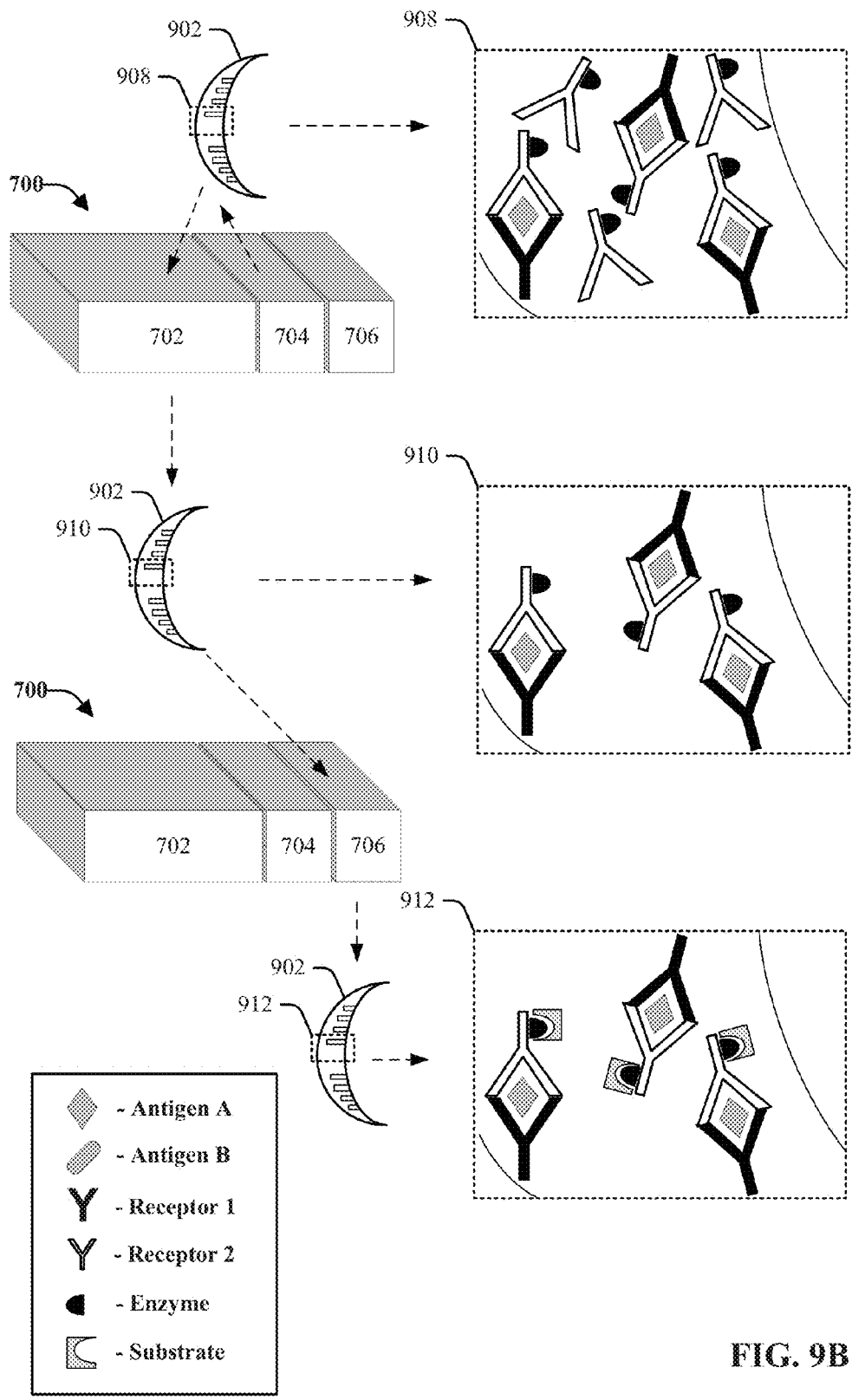

FIGS. 9A-9B present another example application of testing apparatus 700 in accordance with an embodiment. FIG. 9A-9B depict another ELISA based testing of a worn contact lens 902. The testing performed in FIGS. 9A-9B involves a testing apparatus 700 having at least a rinsing compartment 702 and a first detection compartment 704 and a second detection compartment 706. The first detection compartment 704 can include first detector molecules and the second detection compartment 706 can include second detector molecules. According to this example, the first detector molecules comprise detector receptor 2 that is antibody covalently linked to an enzyme. The detector receptor 2 is configured to bind to the one or ligands, antigen A, bound to the one or more Y receptors, receptor 1. The second detector molecules comprise of substrates configured to bind to the enzyme linked to the first detector molecules and produce a signal, such as an appearance of a color.

Initially, a worn contact lens 902 is removed from an eye by a user and placed into the rinsing compartment 702. In this example, the contact lens 902 is a tear collecting contact lens having Y receptors (receptor 1), provided within one or more of the tear collecting cavities. In an aspect, the receptor 1 receptors are antibodies. Box 904 depicts a magnified view of area 904 of the worn contact lens prior to placing the worn contact lens into the rinsing compartment 702. As seen in box 904, some of the receptor 1 receptors are bound to their target ligand, antigen A. Further, some of the receptor 1 receptors remain unbound and some unbound antigen A and antigen B (for which the contact lens does not have a receptor), remains.

Box 906 depicts a magnified view of area 906 of the worn contact lens following rinsing and/or extraction of ligand/receptor complexes of the contact lens 902 in rinsing compartment 702. As seen in box 906, the unbound receptor 1 receptors and unbound antigen A and B are washed away or removed from the contact lens and only the ligand/receptor 1 complexes remain. The washed lens is then placed into first detection compartment 704 comprising the first detection molecules, the receptor 2 receptors. Accordingly, when contact lens 902 is provided within detection compartment 704, the receptor 2 molecules bind with antigen A that is further bound to receptor 1 receptors as a ligand/receptor 1 complex, as seen in the enlarged picture of area 908 of the contact lens at box 908.

Testing is further continued with respect to FIG. 9B. As seen in enlarged area 908 of contact lens 902 following reaction in the first detection compartment 704, some unbound first detector molecules, receptor 2 receptors, remain on/within the contact lens. Accordingly, following placement into the first detection compartment 704, the contact lens 902 is returned to the rinsing compartment 702 for a second rinsing. The second rinsing of the contact lens 902 removes the unbound first detection molecules (e.g. the unbound receptor 2 receptors), as seen in the enlarged picture of area 910, (box 910), of contact lens 902. Lastly, following the second rinsing, the contact lens 902 can be placed into second detection compartment 706. When in the second detection compartment, the second detector molecules, the substrates, bind to their respective enzymes conjugated to the receptor 2 receptors and produce a signal. The binding of the substrates to the enzymes of the receptor 2 receptors is depicted in box 912, an enlarged view of area 912 of contact lens 902. In an aspect, the signal produced in response to binding of the substrates to the enzymes is a visible color that may be observed by a user and or that may be measured using spectroscopic analysis.

FIGS. 10A-13 relate to manufacturing methods of contact lenses disclosed herein. In particular, the manufacturing methods and aspects described with respect to FIGS. 10A-13 can be used to create the disclosed tear collecting contact lenses and/or contact lenses having receptors thereon and/or therein, including contact lenses 110, 120, 130, 140, 150, 210, 220, 320, 330, 340 and the like.

Figure 10A:
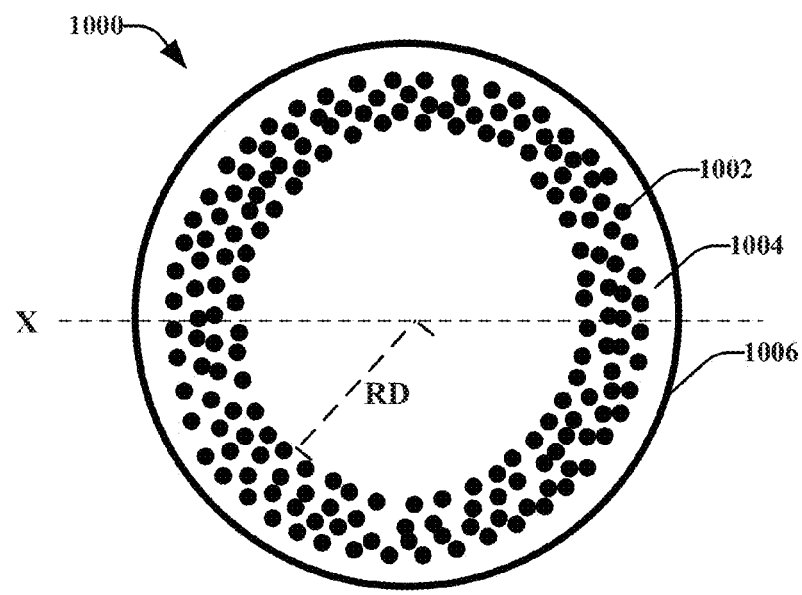
FIGS. 10A, 10B, and 10C illustrate an example contact lens mold for manufacturing a tear collecting contact lens in accordance with various non-limiting embodiments.
Figure 10B:
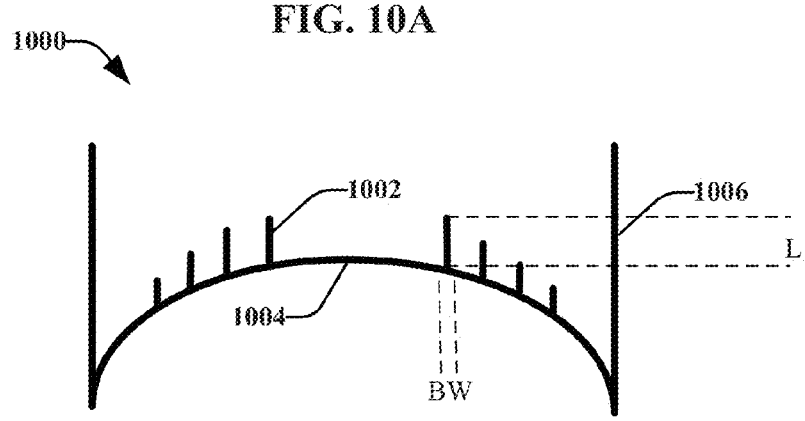
Figure 10C:
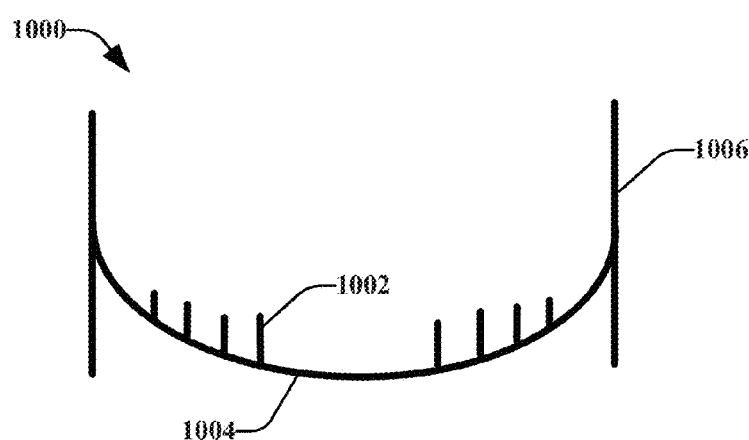

With reference initially to FIGS. 10A, 10B, and 10C presented is an example contact lens mold for use in the manufacturing of contact lenses disclosed herein. FIG. 10A presents a top planar view of a contact lens mold 1000 and FIGS. 10B and 10C present cross-sectional views of contact lens mold 1000 taken along access X of FIG. 10A. As seen in FIG. 10A, contact lens mold 1000 has a mold section having a substantially spherical surface 1004 corresponding to a surface of a contact lens. The surface 1004 of the contact lens mold is the portion of the contact lens mold for receiving a gel substance thereon. In particular, the contact lens mold 1000 is configured to receive a gel material that can later be cured, removed from the contact lens mold, and/or shaped to form a body of a contact lens. In an aspect, contact lens mold 1000 is configured to receive a gel substance that includes but is not limited to: a crosslinked hydrogel comprising hydrophilic monomers (e.g. N-Vinylpyrrolidone, 1-Ethenyl-2-pyrrolidone, N,N-dimethylacrylamide, 2-hydroxyethyl methacrylate, hydroxyethyl acrylate, methacrylic acid and acrylic acid), a strengthening agent, an ultraviolent light (UV) blocker, a tint substance, or a silicone based hydrogel comprising (e.g. crosslinked hydrogels containing silicone macromers and monomers as well as hydrophilic monomers that absorb water).

The surface of the contact lens mold 1004 further has a plurality of protruding structures 1002 extending outwardly from and substantially perpendicular to the surface 1004. The protruding structures 1002 can have any suitable size and shape. For example, the protruding structures can have a cylindrical shape, a square shape, a rectangular shape or a pyramidal shape. In some aspects, the protruding structures 1002 can have a rod, peg or needle shape. The protruding structures 1002 can have a shape such that a length (L) of a rod is greater than a base width (BW) of the rod. The protruding structures 1002 create channels in a gel that is injected into the contact lens mold 1000 following curing and removal of the gel. The protruding structures can have any suitable size and shape so as to create micro channels in a gel injected into the contact lens mold 1000 following curing and removal of the gel. The protruding structures can further be spaced apart such that a gel injected into the contact lens mold 1000 flows around and between the protruding structures. Further, the contact lens mold 1000 can have any number N of protruding structures that facilitate forming a plurality of micro channels.

As seen in FIG. 10A, the contact lens mold can have a circular shape and the protruding structures 1002 can be arranged around the perimeter of the contact lens mold a radial distance (RD) away from the center of the contact lens mold. The RD can be any minimum distance less than the radius of the contact lens mold. As seen in FIGS. 10B and 10C, the protruding structures 1002 can protrude in an outward direction, substantially perpendicular to the surface 1004 of the contact lens mold, such that the protruding structures can be covered with a gel when a gel is received at the surface of the contact lens mold. In an aspect, the surface of the contact lens mold can have a convex shape as seen in FIG. 10B. Still in other aspects, the contact lens mold can have a concave shape as seen in FIG. 10C. It should be appreciated that a contact lens mold having a convex shape can be used to form channels on an inner surface of the contact lens with openings at the inner surface, such as lens 110 in FIG. 1A. Similarly, a contact lens mold having a concave shape can be used to form channels on an outer surface of the contact lens with openings at the outer surface, such as lens 120 in FIG. 1B.

The contact lens mold further comprises a barrier section 1006 around a peripheral edge of the contact lens mold and extending substantially outwardly from the surface in a same direction as the plurality of the protruding structures. The barrier section serves to contain gel that is placed over the contact lens mold surface 1004. In an aspect, the barrier section 1006 has a height greater than a height of any of the plurality of the protruding structures. Contact lens mold 1000 and similar contact lens molds described herein for the use of manufacturing contact lenses can comprise of any suitable material including but not limited to, a metal, a plastic, a ceramic, a photoresist polymer, polymethyl methacrylate, or a combination thereof. In an aspect, the protruding structures and other components of the contact lens mold comprise a same substance. In another aspect, the protruding structures and other components of the contact lens mold comprise different substances.

Figure 11:
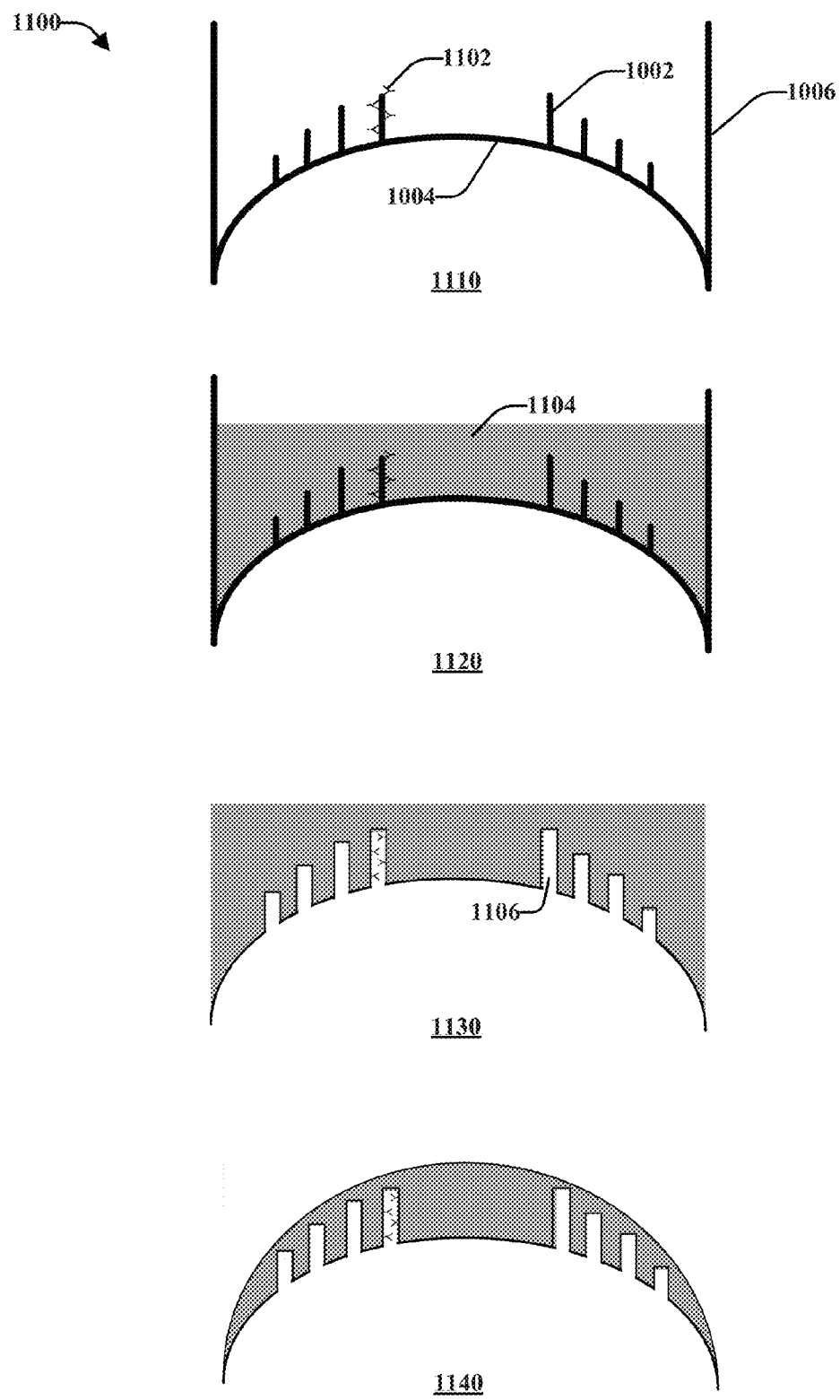
FIG. 11 presents a flow diagram of a method for manufacturing a tear colleting contact lens in accordance with various non-limiting embodiments.

FIG. 11, presents an example flow diagram of a method for manufacturing a tear collecting contact lens in accordance with an embodiment. In an aspect, the manufacturing method employs a contact lens mold, such as contact lens mold 1000 or similar. For example, as seen at 1110, a contact lens mold is provided that includes a plurality of protruding structures protruding structures 1002 protruding substantially perpendicular to a surface 1004 of the contact lens mold and a barrier wall 1006. In an aspect, receptors 1102, such receptors disclosed herein, can be reversibly attached to one or more protruding structures such that the binding site of the receptors is facing and/or attached to the needle. At 1120, the contact lens mold is injected with a gel material 1104, such as silicone hydrogel, which flows around the protruding structures. In particular, the gel material is injected into the contact lens mold in a semi-fluid or gel like state. In some aspects, the gel can include receptors (not shown), such as those described herein, dispersed within the gel. The gel is then allowed time to set and harden.

In an aspect, in order to harden or fix the gel, the gel is cured. Various curing methods can be employed with the disclosed contact lens manufacturing methods. For example, curing of a gel injected into a contact lens mold described herein can include ultraviolet light curing, visible light curing, infrared (IR) curing, thermal curing, and microwave irradiation curing. At 1130, the cured gel is removed from the contact lens mold. The cured gel forms part of a body of the contact lens and comprises one or more channels/cavities 1106 where the protruding structures were. In an aspect, where the protruding structures 1002 of are provided with receptors thereon, the receptors are captured in the gel and remain fixed to or attached to the interior walls of the channels such that the receptors are located.

In an aspect, the contact lens mold may be removed by merely applying a force to separate the contact lens mold and the cured gel. In another aspect, the contact lens mold may comprise a material that can be dissolved in a solution. According to this aspect, the contact lens mold comprising the cured gel can be dipped into a solution that dissolves the contact lens mold and that does not affect the cured gel and/or receptors captured therein. At 1140, the gel comprising the channels 1104, is shaped into the form of a contact lens. For example, the gel can be cut or etched.

Figure 12:
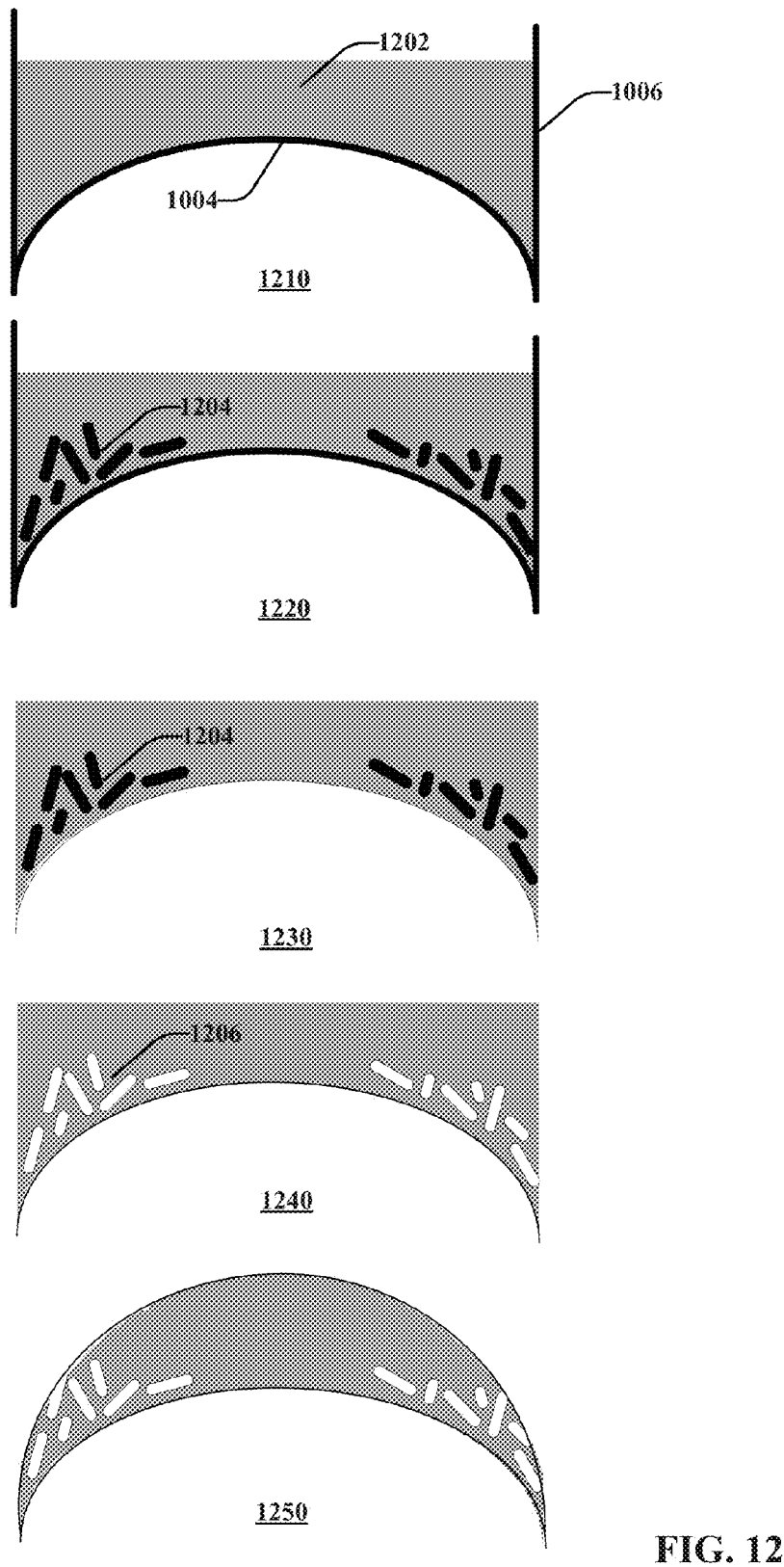
FIG. 12 presents a flow diagram of a method for manufacturing a tear colleting contact lens in accordance with various non-limiting embodiments.

FIG. 12 presents another example flow diagram of a method for manufacturing a tear collecting contact lens in accordance with an embodiment. In an aspect, the manufacturing method employs a contact lens mold, such as a mold similar to that of contact lens mold 1000 yet without the protruding structures. For example, as seen at 1210, a contact lens mold is provided comprising a convex surface 1004 and a bather wall 1006 substantial perpendicular to the surface 1004. The contact lens mold is further injected with a gel material 1202, such as silicone hydrogel. In particular, the gel material 1202 is injected into the contact lens mold in a semi-fluid or gel like state. In an aspect, the gel material is injected into the contact lens mold having suspended structures therein. In another aspect, loose structures 1204 are injected into the gel after the gel is injected into the contact lens mold, such as depicted at 1220. According to this aspect, the structures may be injected into the gel 1202 such that they disperse a radial distance from the center of the contact lens mold.

Structures 1204 can be substantially and shape and size. For example, although the structures are displayed having an ellipsoid shape, the structures may have a rectangular shape, a spherical shape, a triangle shape, and etc. The structures can further be solid or hollow. In some aspects, the structures can include receptors dispersed therein and/or attached to an interior wall thereof, such that the receptors are contained within the structures. In another aspect, the gel 1202 can be injected into the contact lens mold having receptors dispersed therein.

The structures can comprise any material that enables their removal from the gel following setting or hardening of the gel. In particular, the structures can comprise a material that dissolves in a solvent yet does not harm the gel material 1202 and/or receptors therein. In various embodiments the structures 1204 are formed as a polymer structure that is dissolved using a solvent from a hardened and/or cured gel after polymerization. For example, in an aspect, the structures comprise a photoresist polymer. In another aspect, the structures comprise a polymethyl methacrylate (PMMA). Additional polymer materials from which the structures 1204 can be made include but are not limited to: polylactic acid, polyglycolic acid (and related copolymers), polyvinyl alcohol (PVA), polysaccharides (i.e. CMC, HA, chitosan), polyanhydrides, polyvinyl pyrollidone, and polystyrene. Example solvents that can be employed to dissolve a rod 1204 can include but are not limited to: water, a dilute aqueous base, acetone, or toluene. In an aspect, where the structures 1204 comprise PVA, polysaccarides, or polyvinyl pyrollidone an appropriate solvent is water. In another aspect, where the structures 1204 comprise polylactic acid, polyglycolic acid (and related copolymers), or polyanhydrides, an appropriate solvent is a dilute aqueous base. Still in yet another aspect, where the structures 1204 comprise PMMA or polystyrene, an appropriate solvent is acetone or toluene.

After the gel 1202 and the structures 1204 are provided within the contact lens mold, the gel is allowed time to set and harden. In an aspect, in order to harden or set the gel, the gel is cured with any of the various curing methods disclosed herein, such as with ultraviolet light. At 1230, the cured gel is removed from the contact lens mold. In an aspect, the contact lens mold may be removed by merely applying a force to separate the contact lens mold and the cured gel. According to this aspect, the structures must further be removed from the cured gel at 1240. At 1240, the structures are removed from the gel by dissolving the structures in an appropriate solvent that does not harm the cured gel and/or the receptors therein. The cured gel forms part of a body of the contact lens and comprises one or more cavities 1206 where the structures were. In another aspect, the contact lens mold may also comprise a material that can be dissolved in a solvent. According to this aspect, the contact lens mold comprising the cured gel and structures therein can be dipped into a solvent that dissolves the contact lens mold and the structures 1204 and that does not affect the cured gel and/or receptors captured therein. At 1250, the gel comprising the cavities 1206, is shaped into the form of a contact lens. For example, the gel can be cut or etched.

Figure 13:
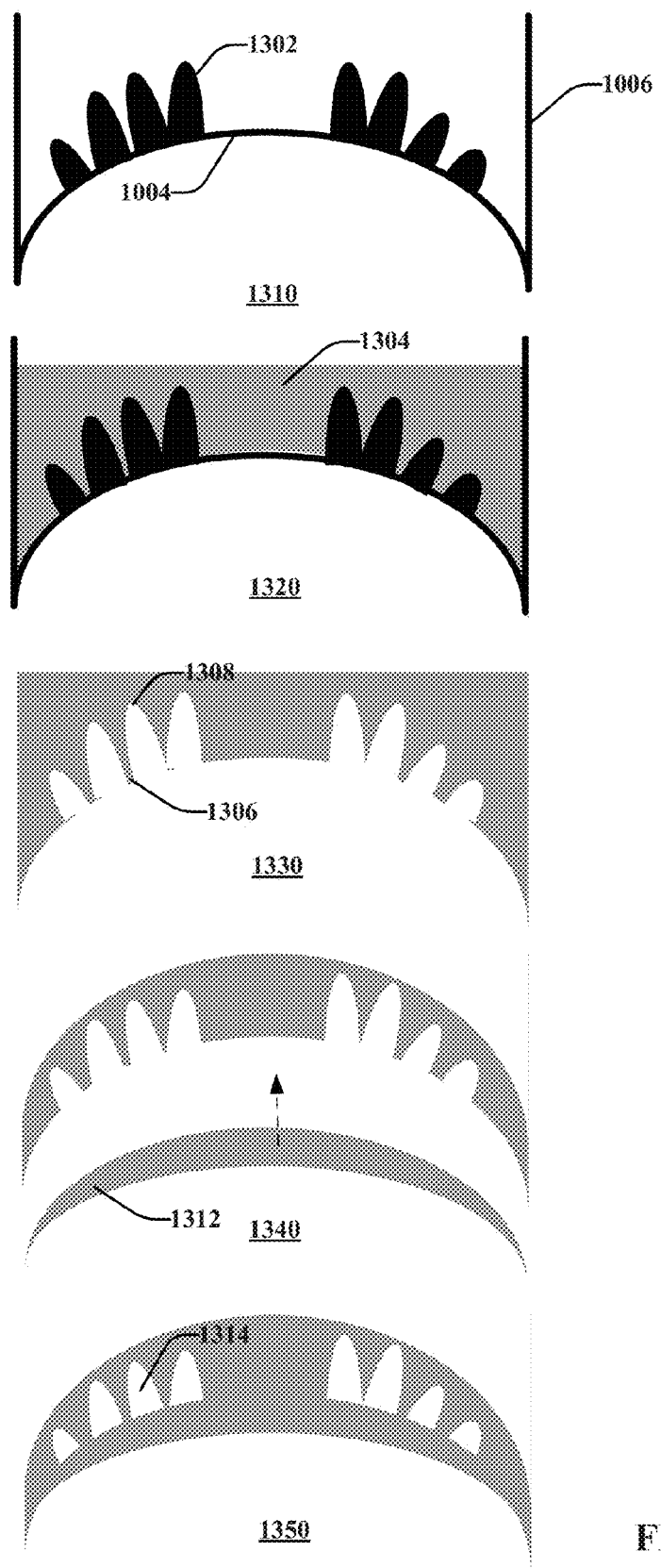
FIG. 13 presents a flow diagram of a method for manufacturing a tear colleting contact lens in accordance with various non-limiting embodiments.

FIG. 13, presents another example flow diagram of a method for manufacturing a tear collecting contact lens in accordance with an embodiment. In an aspect, the manufacturing method employs a contact lens mold similar to mold 1000 yet without the needles. Rather than structures, at 1310, a contact lens mold is provided with a surface 1004 having a plurality of raised bumps 1302 such that the surface of the surface comprises peaks and valleys associated with the bumps. In an aspect, receptors, such receptors disclosed herein, can be reversibly attached to one or more of the bumps 1302 (not shown) such that the binding site of the receptors is facing and/or attached to the bump. At 1320, the contact lens mold is injected with a gel material 1304, such as silicone hydrogel, which flows around the bumps. In particular, the gel material is injected into the contact lens mold in a semi-fluid or gel like state. In some aspects, the gel can include receptors (not shown), such as those described herein, dispersed within the gel. The gel is then allowed time to set and harden. In an aspect, in order to harden or fix the gel, the gel is cured (e.g. with ultraviolet light, heat, or other curing methods disclosed herein). At 1330, the cured gel is removed from the contact lens mold. In some aspects, after the cured gel is removed, one or more receptors having an affinity for a known ligand can be injected into the negative space created in the cured gel where the bumps were, (e.g. the peaks 1306 and valleys 1308). The cured gel forms part of a body of the contact lens and has a cross-section comprising of peaks 1306 and valleys 1308 corresponding to the bumps. In an aspect, where the bumps 1302 are provided with receptors thereon, the receptors are captured in the gel and remain fixed to or attached to the interior walls of the gel in the spaces where the bumps were (not shown).

In an aspect, the contact lens mold may be removed by merely applying a force to separate the contact lens mold and the cured gel. In another aspect, the contact lens mold may comprise a material that can be dissolved in a solution. According to this aspect, the contact lens mold comprising the cured gel can be dipped into a solution that dissolves the contact lens mold and that does not affect the cured gel and/or receptors captured therein. At 1340 the cured gel cured gel is combined with a substrate 1312 having a substantially flat cross-section to form a part of a body of the contact lens. In some aspects where the receptors are provided within the peaks and valleys of the cured gel, the receptors can become trapped within the formed channels following combination of the cured gel with the substrate. At 1350, the contact lens may be further molded, cut and/or etched to form a final contact lens. As seen at step 1350, the body of the resulting contact has a cross-section with one or more channels 1314 corresponding to the plurality of raised bumps.

FIGS. 14-18 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 14:
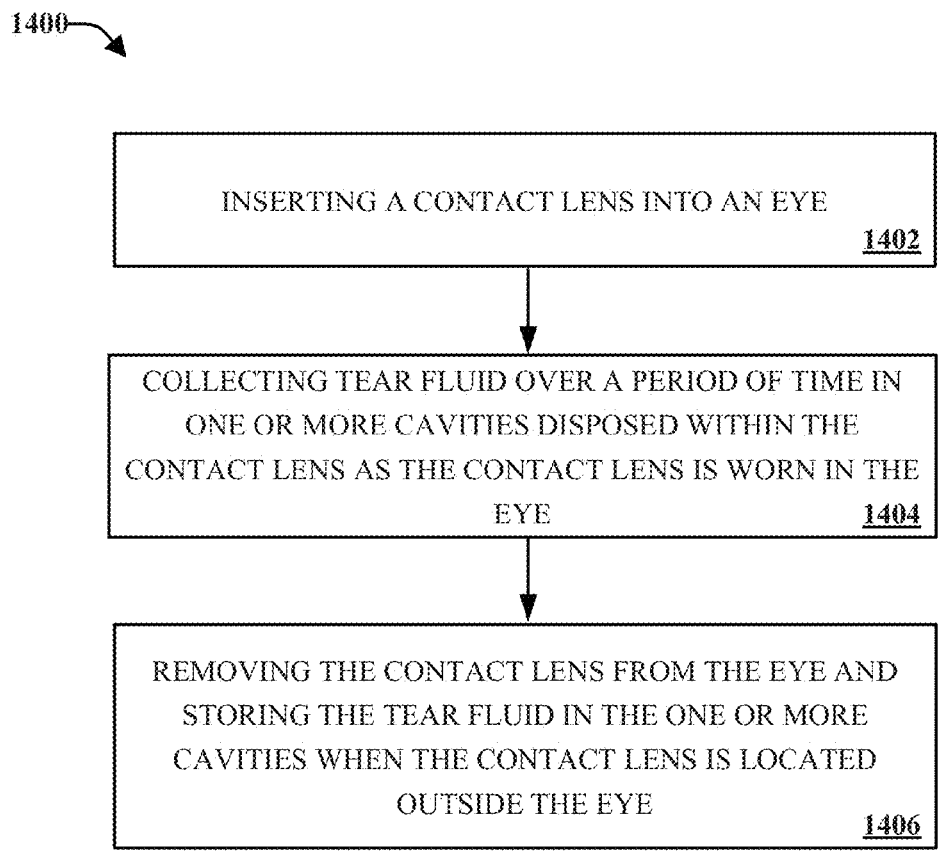
FIG. 14 illustrates an example methodology for collecting tear fluid with a contact lens in accordance with various aspects and implementations described herein.

Referring now to FIG. 14, presented is a flow diagram of an example application of systems an apparatuses disclosed in this description accordance with an embodiment. In an aspect, in exemplary methodology 1400, a tear collecting contact lens as disclosed herein in employed by a user in order to collect tears therein. At 1402, a contact lens is inserted into an eye (e.g. contact lens 110, 120, 130, 140, 150, 210, 220, 320, 330, 340 and the like). At 1404, tear fluid is collected over a period of time in one or more cavities disposed within the contact lens as the contact lens is worn in the eye. At 1406, the contact lens is removed from the eye and the tear fluid is stored in the one or more cavities when the contact lens is located outside the eye.

Figure 15:
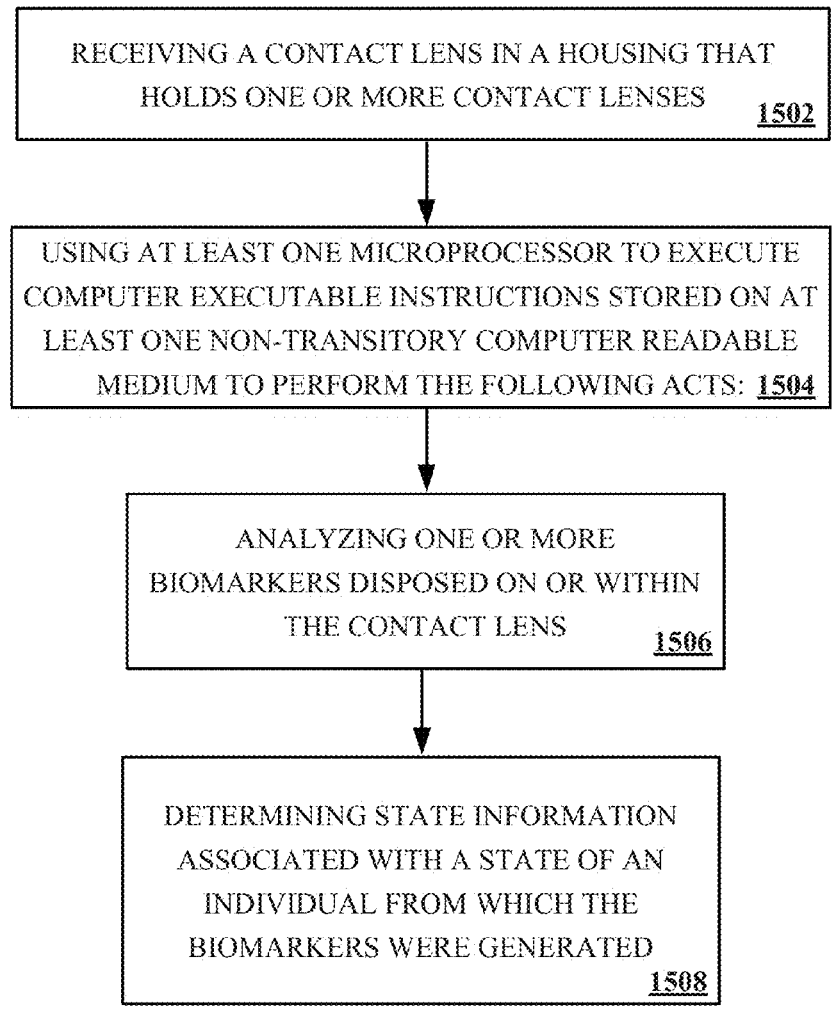
FIG. 15 illustrates an example methodology for testing a contact lens in accordance with various aspects and implementations described herein.

Referring to FIG. 15, presented is another flow diagram of an example application of systems an apparatuses disclosed in this description accordance with an embodiment. In an aspect, in exemplary methodology 1500, a contact lens testing apparatus (e.g. apparatus 600) utilizes a processor to execute computer executable instructions to perform functions. At 1502, a contact lens is received in a housing that holds one or more contact lenses (e.g. housing 502 and/or testing compartment 510). At 1504 at least one microprocessor (e.g. processor 610) is used to execute computer executable instructions stored on at least one non-transitory computer readable medium (e.g. memory 612) to perform the following acts: analyzing one or more biomarkers disposed on or within the contact lens (e.g. using analysis component 608) 1506 and determining state information associated with a state of an individual from which the biomarkers were generated (e.g. using analysis component 608) 1508.

Figure 16:
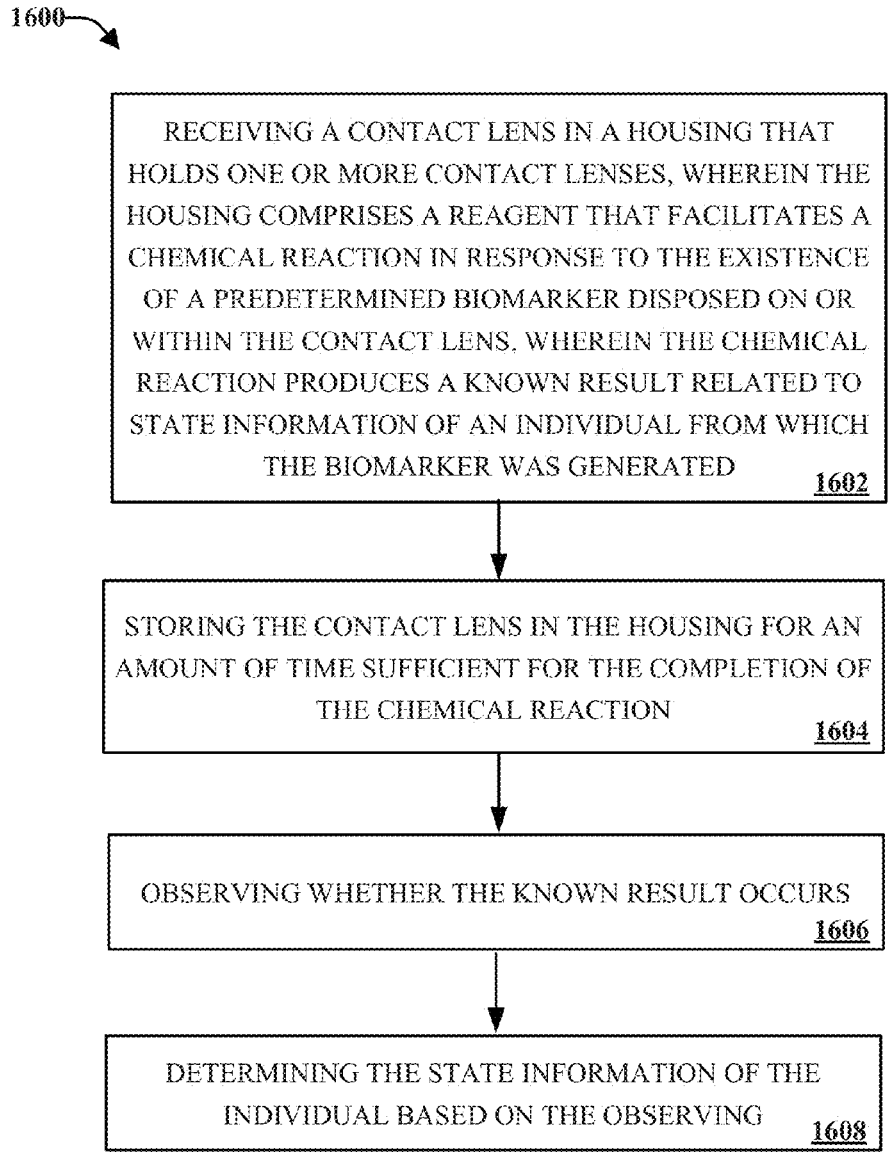
FIG. 16 illustrates another example methodology for testing a contact lens in accordance with various aspects and implementations described herein.

Referring to FIG. 16, presented is another flow diagram of an example application of systems an apparatuses disclosed in this description accordance with an embodiment. In an aspect, in exemplary methodology 1600, a contact lens testing apparatus (e.g. apparatus 500) is used to test a worn contact lens for a predetermined substance. At 1602, a contact lens is received in a housing that holds one or more contact lenses (e.g. housing 502). The housing comprises a reagent that facilitates a chemical reaction in response to the existence of a predetermined biomarker disposed on or within the contact lens. The chemical reaction produces a known result related to state information of an individual from which the biomarker was generated. At 1604, the contact lens is stored in the housing for an amount of time sufficient for the completion of the chemical reaction. At 1606, an individual can observe whether the known result occurs 1606. Further, at 1608, the individual can determine the state information based on the observing. For example, the individual may determine that he/she has a high glucose level in response to the contact lens turning blue following the chemical reaction. In an aspect, when apparatus 600 is employed, the analysis component 608 can perform observation of the chemical reaction and determination of state information associated with observed results.

Referring to FIG. 17, presented is another flow diagram of an example application of systems an apparatuses disclosed in this description accordance with an embodiment. In an aspect, in exemplary methodology 1700, a contact lens comprising receptors as disclosed herein in employed by a user in order to collect predetermined ligands. At 1702, a contact lens is inserted into an eye (e.g. contact lens 320, 330, 340 and the like). The contact lens comprises one or more receptors disposed on or within a substrate of the contact lens. The one or more receptors are configured to bind to a known ligand. At 1704, one or more known ligands are received at the one or more receptors, wherein the received ligands bind to the one or more receptors. At 1706, the contact lens is removed from the eye with the one or more known ligands bound to the one or more receptors.

Figure 18:
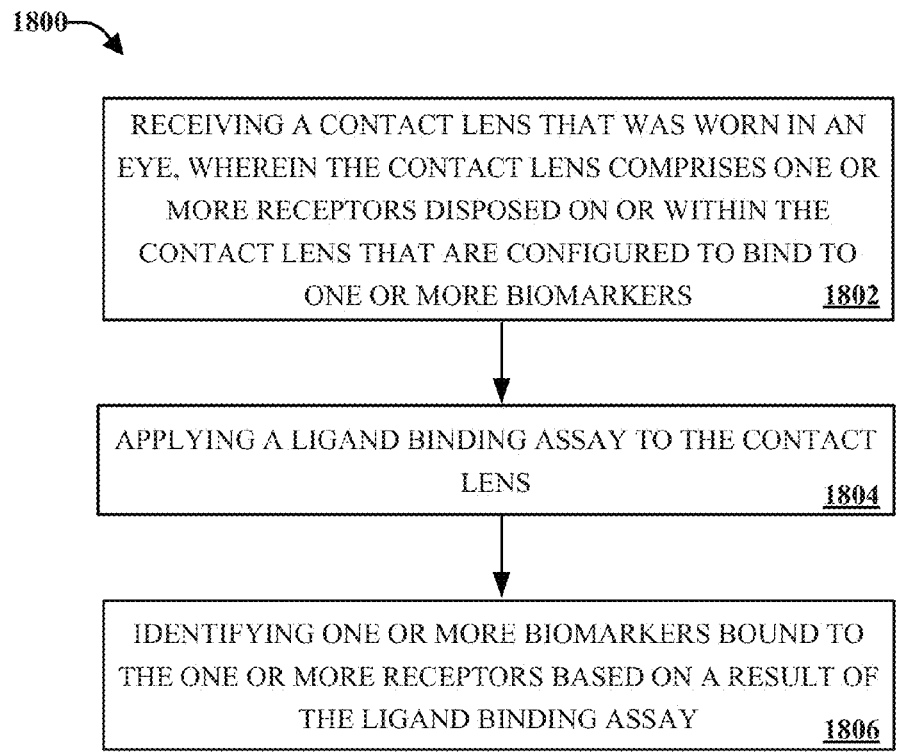
FIG. 18 illustrates another example methodology for testing a contact lens in accordance with various aspects and implementations described herein.

Referring to FIG. 18, presented is another flow diagram of an example application of systems an apparatuses disclosed in this description accordance with an embodiment. In an aspect, in exemplary methodology 1800, a contact lens testing apparatus (e.g. apparatus 700) utilizes a processor to execute computer executable instructions to perform functions. At 1802, a contact lens that was worn in an eye is received (e.g. using housing 502 and/or testing compartment 510). The received contact lens comprises one or more receptors disposed on or within the contact lens that are configured to bind to one or more biomarkers. At 1804, a ligand binding assay is applied to the contact lens (e.g. using testing compartment 510). At 1806, one or more biomarkers are identified that are bound to the one or more receptors based on a result of the ligand binding assay (e.g. using human observation and/or analysis component 608).

Exemplary Networked and Distributed Environments

Figure 19:
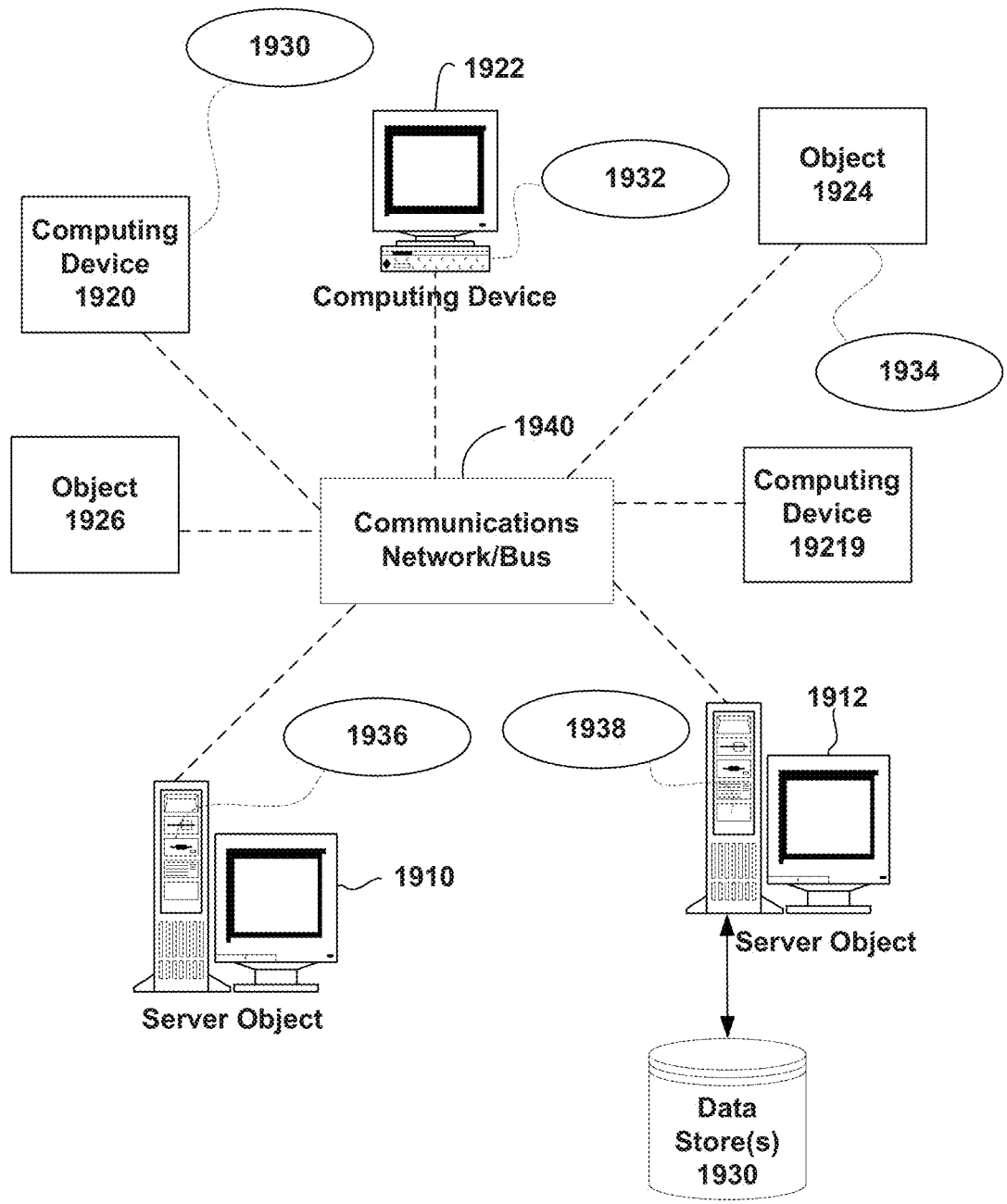
FIG. 19 is an illustration of a schematic diagram of an exemplary networked or distributed computing environment with which one or more aspects described herein can be associated.

FIG. 19 provides a schematic diagram of an exemplary networked or distributed computing environment with which one or more aspects described in this disclosure can be associated. The distributed computing environment includes computing objects 1910, 1912, etc. and computing objects or devices 1920, 1922, 1924, 1926, 1928, etc., which can include programs, methods, data stores, programmable logic, etc., as represented by applications 1930, 1932, 1934, 1936, 1938. It can be appreciated that computing objects 1910, 1912, etc. and computing objects or devices 1920, 1922, 1924, 1926, 1928, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 1910, 1912, etc. and computing objects or devices 1920, 1922, 1924, 1926, 1928, etc. can communicate with one or more other computing objects 1910, 1912, etc. and computing objects or devices 1920, 1922, 1924, 1926, 1928, etc. by way of the communications network 1940, either directly or indirectly. Even though illustrated as a single element in FIG. 19, network 1940 can include other computing objects and computing devices that provide services to the system of FIG. 19, and/or can represent multiple interconnected networks, which are not shown. In a network environment in which the communications network/bus 1940 can be the Internet, the computing objects 1910, 1912, etc. can be Web servers, file servers, media servers, etc. with which the client computing objects or devices 1920, 1922, 1924, 1926, 1928, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or the testing devices described herein. In various aspects, the data store can include or be included within, any of the memory described herein, any of the contact lenses described herein and/or the testing devices described herein. In various aspects, the data store can be any repository for storing information transmitted to or received from the contact lens.

Figure 20:
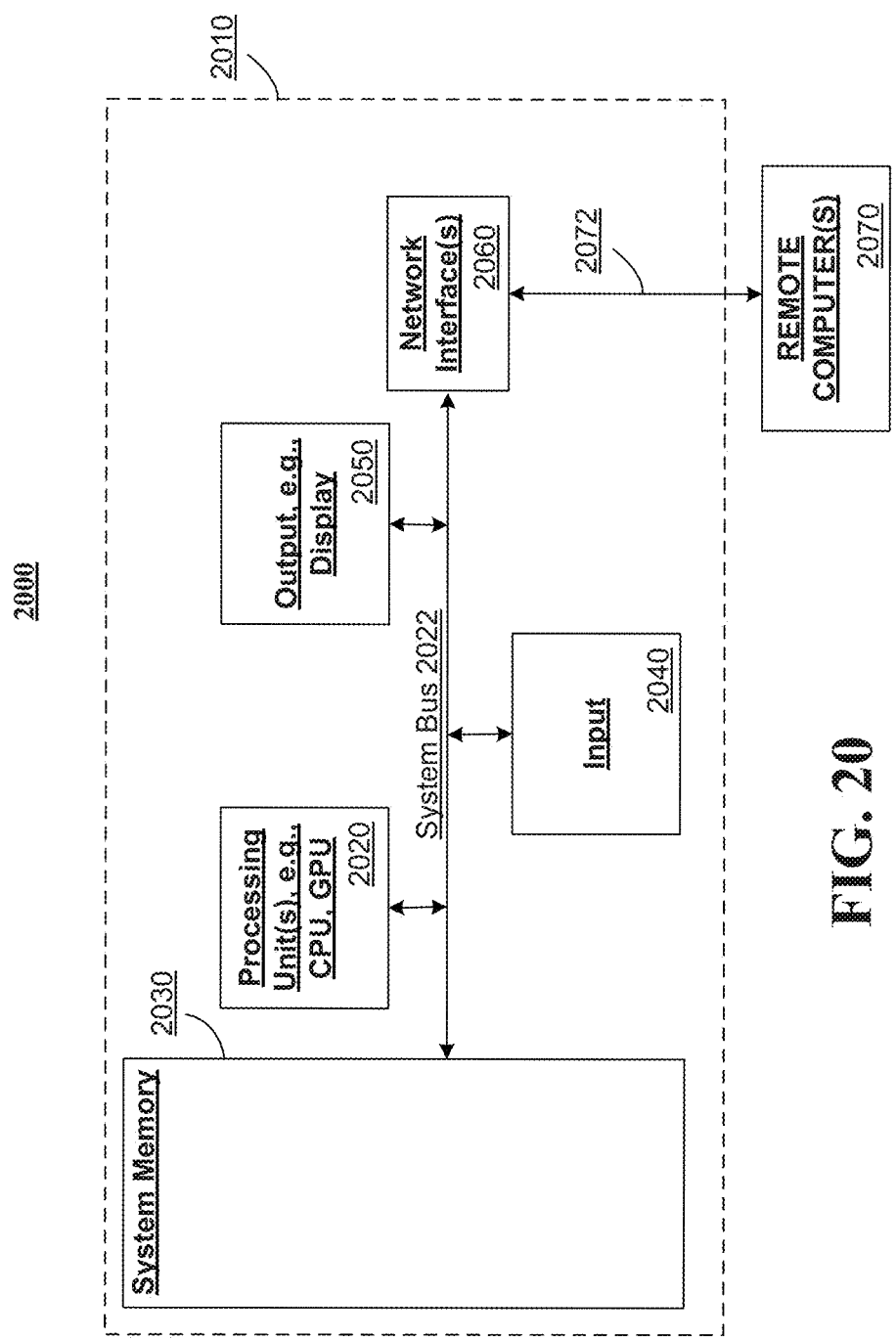
FIG. 20 is an illustration of a schematic diagram of an exemplary computing environment with which one or more aspects described herein can be associated.

FIG. 20 illustrates an example of a suitable computing system environment 2000 in which one or aspects of the aspects described in this disclosure can be implemented. Components of computer 2010 can include, but are not limited to, a processing unit 2020, a system memory 2030, and a system bus 2022 that couples various system components including the system memory to the processing unit 2020. Computer 2010 typically includes a variety of computer readable media and can be any available media that can be accessed by computer 2010. The system memory 2030 can include computer storage media in the form of volatile and/or nonvolatile memory such as read only memory (ROM) and/or random access memory (RAM). By way of example, and not limitation, memory 2030 can also include an operating system, application programs, other program components, and program data.

A user can enter commands and information into the computer 2010 through input devices 2040 (e.g., keyboard, keypad, a pointing device, a mouse, stylus, touchpad, touch screen, motion detector, camera, microphone or any other device that allows the user to interact with the computer 2010). A monitor or other type of display device can be also connected to the system bus 2022 via an interface, such as output interface 2050. In addition to a monitor, computers can also include other peripheral output devices such as speakers and a printer, which can be connected through output interface 2050.

The computer 2010 can operate in a networked or distributed environment using logical connections to one or more other remote computers, such as remote computer 2060. The remote computer 2060 can be a personal computer, a server, a router, a network PC, a peer device or other common network node, or any other remote media consumption or transmission device, and can include any or all of the elements described above relative to the computer 2010. The logical connections depicted in FIG. 20 include a network 2070, such as a local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A device comprising:
   a housing configured to hold one or more contact lenses; and
   a testing component disposed within the housing that is configured to test for presence of one or more biomarkers bound to one or more receptors disposed in one or more cavities formed at predetermined locations within a body of a contact lens placed within the testing component and to facilitate determining state information associated with a state of an individual from which the biomarkers were generated, wherein the one or more cavities have openings on an inner surface or outer surface of the contact lens and have depths less than a thickness of the contact lens.

2. The device of claim 1, wherein the one or more biomarkers bound to the one or more receptors are located in tear fluid generated by the individual and held within the one or more cavities.

3. The device of claim 2, further comprising, an extraction component disposed within the housing and configured to extract the tear fluid comprising the one or more biomarkers bound to one or more receptors disposed in the one or more cavities without disrupting bonds between the one or more biomarkers and the one or more receptors.

4. The device of claim 1, the testing component further comprising:
   a rinsing compartment comprising a rinsing solution and configured to remove at least one of unbound biomarkers or unbound receptors from the contact lens when the contact lens is provided therein.

5. The device of claim 1, the testing component further comprising:
   a detection compartment comprising detector molecules configured to bind to the one or more receptors having the one or more biomarkers bound thereto and produce a signal in response to binding when the contact lens is placed within the detection compartment.

6. The device of claim 1, the testing component further comprising:
   a detection compartment comprising detector molecules configured to bind to the one or biomarkers bound to the one more receptors and produce a signal in response to binding when the contact lens is placed within the detection compartment.

7. The device of claim 6, wherein the detector molecules include first detector molecules comprising a detector antibody covalently linked to an enzyme, the detector antibody configured to bind to the one or biomarkers bound to the one or more receptors, and second detector molecules comprising a substrate configured to bind to the enzyme to produce the signal.

8. The device of claim 7, the testing component further comprising:
   a first detection compartment comprising first detector molecules;
   a second detection compartment comprising second detector molecules; and
   a rinsing compartment comprising a rinsing solution that removes unbound biomarkers and unbound first detector molecules from the contact lens when the contact lens is provided therein.

9. The device of claim 1, wherein the state information includes at least one of a glucose level, alcohol level, histamine level, urea level, lactate level, cholesterol level, sodium ion level, potassium ion level, calcium ion level or magnesium ion level of the individual.

10. The device of claim 1, further comprising:
    a control component configured to control testing carried out in the device.

11. The device of claim 1, wherein the one or more receptors include a first receptor and a second receptor, wherein the one or more cavities include a first cavity and a second cavity, and wherein the first receptor is disposed in the first cavity and the second receptor is disposed in the second cavity.

12. The device of claim 1, wherein the one or more cavities include a first cavity having an opening on the inner surface of the contact lens and a second cavity having an opening on the outer surface of the contact lens.

* * * * *